US008853200B2

(12) United States Patent
Grainger et al.

(10) Patent No.: US 8,853,200 B2
(45) Date of Patent: Oct. 7, 2014

(54) TREATMENT OF RHEUMATOID ARTHRITIS WITH 3-AMINO LACTAM COMPOUNDS

(75) Inventors: David John Grainger, Cambridge (GB); David Fox, Banbury (GB)

(73) Assignee: Cambridge Enterprise Limited, Cambridge (GB)

( * ) Notice: Subject to any disclaimer, the term of this patent is extended or adjusted under 35 U.S.C. 154(b) by 665 days.

(21) Appl. No.: 12/671,785

(22) PCT Filed: Aug. 1, 2008

(86) PCT No.: PCT/GB2008/002635
§ 371 (c)(1),
(2), (4) Date: Sep. 1, 2010

(87) PCT Pub. No.: WO2009/016390
PCT Pub. Date: Feb. 5, 2009

(65) Prior Publication Data
US 2010/0324089 A1  Dec. 23, 2010

(30) Foreign Application Priority Data
Aug. 2, 2007  (GB) .................................. 0715068.3

(51) Int. Cl.
*A61K 31/55*   (2006.01)
*C07D 223/10*  (2006.01)
*A61P 29/00*   (2006.01)
*A61P 19/10*   (2006.01)
*C07D 211/76*  (2006.01)
*C07D 223/12*  (2006.01)
*A61K 31/45*   (2006.01)

(52) U.S. Cl.
CPC .............. *A61K 31/45* (2013.01); *C07D 211/76* (2013.01); *C07D 223/12* (2013.01)
USPC ...................................... 514/212.03; 540/527

(58) Field of Classification Search
None
See application file for complete search history.

(56) References Cited

U.S. PATENT DOCUMENTS

| 5,593,827 | A | 1/1997 | Bycroft et al. |
| 5,776,974 | A | 7/1998 | Bycroft et al. |
| 5,969,158 | A | 10/1999 | Bycroft et al. |
| 6,395,282 | B1 | 5/2002 | Kende et al. |
| 6,544,981 | B2 | 4/2003 | Stein et al. |
| 6,602,905 | B1 | 8/2003 | Gardiner et al. |
| 7,662,967 | B2 | 2/2010 | Grainger et al. |
| 7,897,620 | B2 * | 3/2011 | Grainger et al. ............ 514/315 |
| 2006/0233728 | A1 | 10/2006 | Sagawa et al. |

FOREIGN PATENT DOCUMENTS

| EP | 0443588 A1 | 8/1991 |
| EP | 0519877 A1 | 12/1992 |
| GB | 1374365 | 11/1974 |
| GB | 2452696 A | 3/2009 |
| JP | 04-211089 A | 8/1992 |
| JP | 10265761 A | 10/1998 |
| WO | 89/10961 A1 | 11/1989 |
| WO | 95/01175 A1 | 1/1995 |
| WO | 98/25951 A1 | 6/1998 |
| WO | 99/12933 A3 | 3/1999 |
| WO | 99/12968 A3 | 3/1999 |
| WO | 99/27786 A1 | 6/1999 |
| WO | 99/31506 A1 | 6/1999 |
| WO | 99/31507 A1 | 6/1999 |
| WO | 00/35871 A1 | 6/2000 |
| WO | 01/26650 A3 | 4/2001 |
| WO | 01/68655 A3 | 9/2001 |
| WO | 02/052949 A1 | 7/2002 |
| WO | 2004/022536 A1 | 3/2004 |
| WO | 2005/053702 A3 | 6/2005 |
| WO | 2005/075439 A1 | 8/2005 |
| WO | 2006/016152 A1 | 2/2006 |
| WO | 2006/018609 A2 | 2/2006 |
| WO | 2006/024815 A1 | 3/2006 |
| WO | 2006/076442 A3 | 7/2006 |
| WO | 2006/085096 A1 | 8/2006 |
| WO | 2006/134378 A1 | 12/2006 |
| WO | 2006/134384 A1 | 12/2006 |
| WO | 2006/134385 A3 | 12/2006 |

OTHER PUBLICATIONS

PDF copy regarding rheumatoid arthritis from Medicine Net (http://www.medicinenet.com/rheumatoid_arthritis/page2htm, 2012).*
Gullick et al. New therapies for the treatment of systemic lupus erythematosus. Expert Opin. Ther. Patents (2007), 17(3): 299-313.*
Appel & Valeri. The course and treatment of lupus nephritis. Annu. Rev. Med. 1994, 45: 525-37.*
Kuhn et al. Cutaneous lupus erythematosus: update of therapeutic options. J. Am. Acad. Dermatol. 2011, 65: e195-213.*
Antonov et al. Drug-induced lupus erythematosus. Clinics in Dermatology, 2004; 22: 157-166.*
International Application No. PCT/GB2006/002218 International Search Report and Written Opinion mailed Dec. 14, 2006, 16 pages.
Grainger, et al. "Broad Spectrum Chemokine Inhibitors Related to NR58-3.14.3", Mini-Reviews in Medicinal Chemistry, 2005, vol. 5, pp. 825-883.
Clarke, et al. "Synthesis and Mass Spectra of Some 3-Acylamino-2-piperidones", J. Chem. Soc. C: Organic, 1971, pp. 3743-3748.
Gao, et al. "Catalytic Asymmetric Synthesis of a Potential Thiomarinol Antibiotic", J. Am. Chem. Soc., Feb. 16, 2005, vol. 127(6), pp. 1628-1629.
Batkrakov, et al. "A new Ornithine-Containing Lipid From Actinomyces No. 660-15", Chemistry of Natural Compounds, Mar. 1974, vol. 8(2), pp. 153-158.
Jiao, et al. "Structural Identification of Cepaciamide A, a Novel Fungitoxic Compound from Pseudomonas cepacia D-202", Tetrahedron Letters, 1996, vol. 37(7), pp. 1039-1042.
Schreiber, et al. "The Reaction of Cyanogen Bromide with Mono- and Diamino Acids", Journal of the American Chemical Society, Jun. 20, 1964, vol. 86(12), pp. 2441-2445.

(Continued)

*Primary Examiner* — Anna Pagonakis
(74) *Attorney, Agent, or Firm* — VLP Law Group LLP; Richard G. A. Bone

(57) ABSTRACT

The invention relates to 3-(2',2'-dimethylpropanoylamino)-tetrahydropyridin-2-one, and its pharmaceutical compositions and its use for preparing a medicament intended to prevent or treat inflammatory disorders.

2 Claims, 21 Drawing Sheets

(56) References Cited

OTHER PUBLICATIONS

Figure 1A:
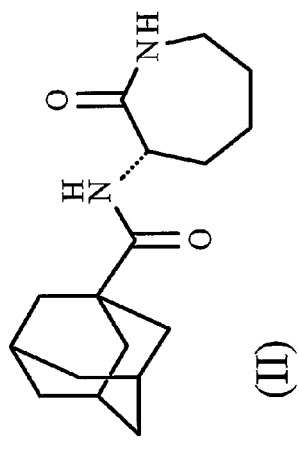
Figure 1A:
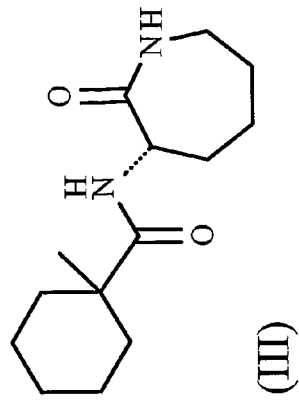
Figure 1A:
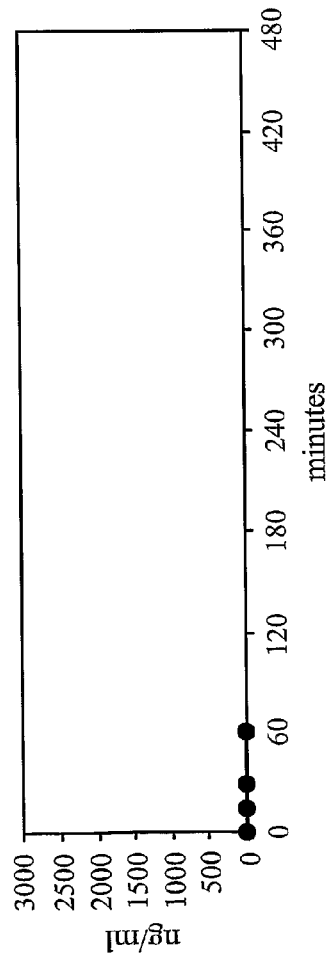
Figure 1B:
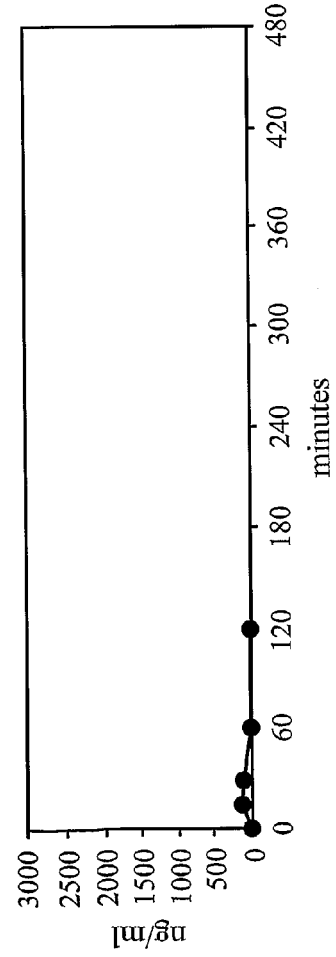
Figure 1C:
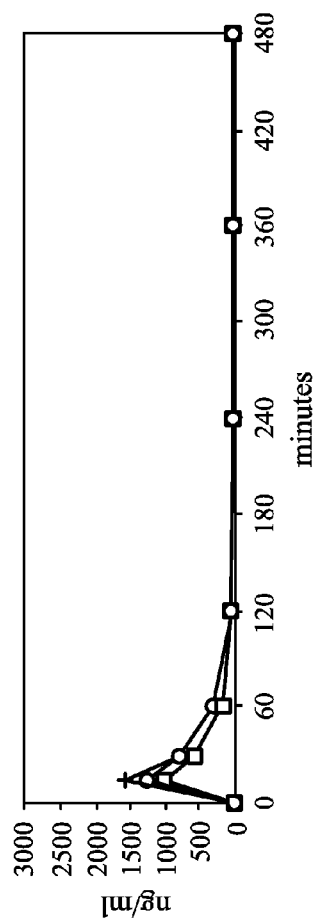
Figure 1C:
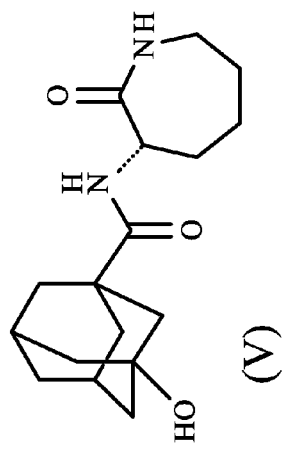
Figure 1D:
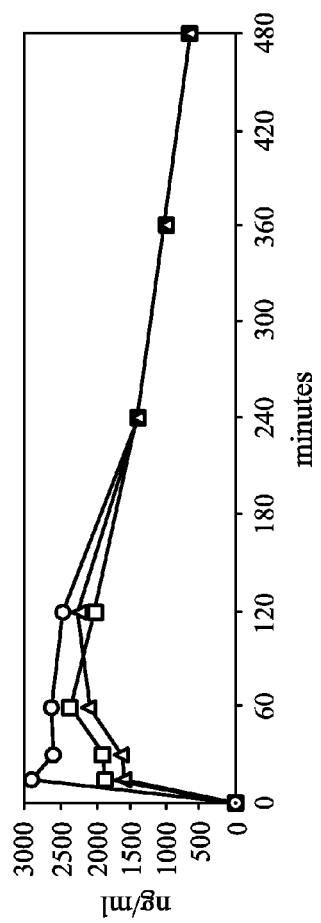
Figure 1D:
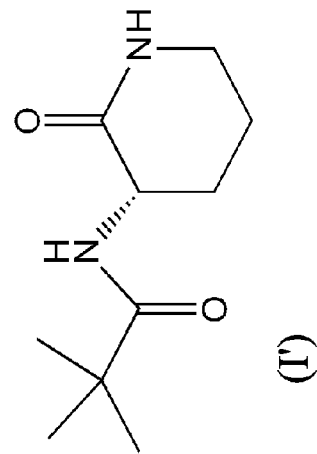
Figure 1E:
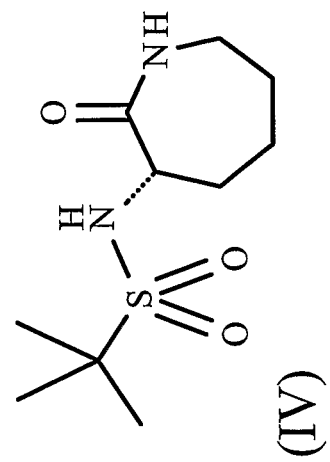
Figure 1E:
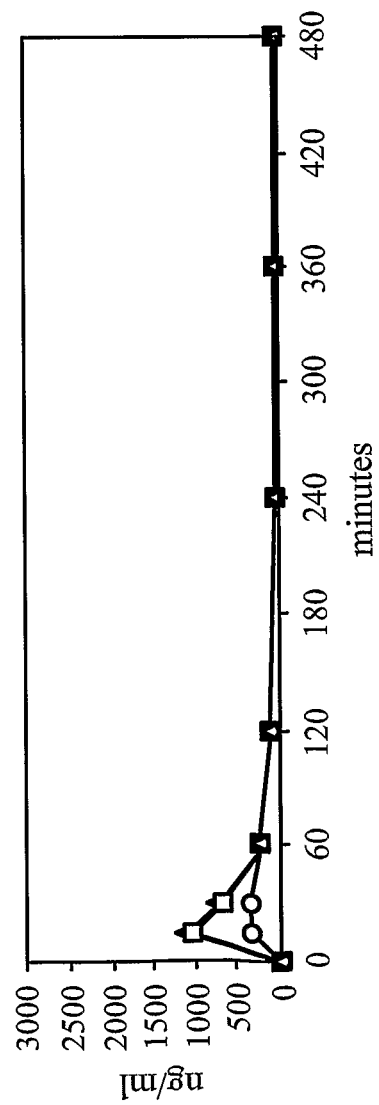

Fringuelli, et al. "Synthesis and evaluation of anti-apoptotic activity of L-carnitine cyclic analogues and amino acid derivatives", II Farmaco, Apr. 4, 2004, vol. 59(4), pp. 271-277.

Cotman, et al. "A Potential Role for Apoptosis in Neurodegeneration and Alzheimer's Disease", Molecular Neurobiology, 1995, vol. 10(1), pp. 19-45.

Fox, et al. "Design, Synthesis, and Preliminary Pharmacological Evaluation of N-Acyl-3-aminoglutarimides as Broad-Spectrum Chemokine Inhibitors in Vitro and Anti-inflammatory Agents in Vivo", J. Med. Chem., 2002, vol. 45, pp. 360-370.

Fox, et al. "Identification of 3-(Acylamino)azepan-2-ones as Stable Broad-Spectrum Chemokine inhibitors Resistant to Metabolism in Vivo", J. Med. Chem., 2005, vol. 48, pp. 867-874.

Frow, et al. "Tools for Anti-Inflammatory Drug Design: In Vitro Models of Leukocyte Migration", Medicinal Research Reviews, 2004, vol. 24, No. 3, pp. 267-298.

Grainger, et al. "Broad-spectrum chemokine inhibitors (BSCIs) and their anti-inflammatory effects in vivo", Biochemical Pharmacology, 2003, vol. 65, pp. 1027-1034.

Reckless, et al. "Identification of oligopeptide sequences which inhibit migration induced by a wide range of chemokines", Biochem. J., 1999, vol. 340, pp. 803-811.

Reckless, et al. "The pan-chemokine inhibitor NR58-3.4.3 abolishes tumour necrosis factor-$\alpha$ accumulation and leucocyte recruitment induced by lipopolysaccaride in vivo", Immunology, 2001, vol. 103, No. 2, pp. 244-254.

Gould, "Salt selection for basic drugs", International Journal of Pharmaceutics, 1986, vol. 33, pp. 201-217.

International Application No. PCT/GB2008/002635 International Search Report and Written Opinion mailed Oct. 9, 2008, 16 pages.

R343889 [N-(2-Oxo-Piperidin-3-yl)-isobutyramide]; Sigma-Aldrich Catalog, available at http://www.sigmaaldrich.com/catalog/search/ProductDetail/ALDRICH/R343889?PrtP (last accessed, Jul. 28, 2007).

Hizawa, N., "Genetic Backgrounds of Asthma and COPD", Allergology Int'l. 58, 315-322 (2009).

Postma, D. S., and Boezen, H. M., "Rationale for the Dutch Hypothesis", Chest, 126(2), Supplement 96-104, Aug. 2004.

Ruse, C. E., and Parker, S. G., "Genetics and the Dutch Hypothesis", Chronic Respiratory Disease 1:105-113 (2004).

Welte, T., and Groneberg, D. A., "Asthma and COPD", Experimental and Toxicologic Pathology 57 S2, 35-40 (2006).

File History for Supplemental Examination/ex parte re-examination No. 96/030,000, as filed for U.S. Pat. No. 7,662,967 ("Anti-Inflammatory Compounds and Compositions").

File History for Supplemental Examination No. 96/030,001, as filed for U.S. Pat. No. 7,987,620 ("Methods of Using Anti-Inflammatory Compounds").

\* cited by examiner (II)

(III)

(IV)

TREATMENT OF RHEUMATOID ARTHRITIS WITH 3-AMINO LACTAM COMPOUNDS

The invention relates to 3-(2',2'-dimethylpropanoylamino)-tetrahydropyridin-2-one, and its pharmaceutical compositions and its use for preparing a medicament intended to prevent or treat inflammatory disorders.

Inflammation is an important component of physiological host defence. Increasingly, however, it is clear that temporally or spatially inappropriate inflammatory responses play a part in a wide range of diseases, including those with an obvious leukocyte component (such as autoimmune diseases, asthma or atherosclerosis) but also in diseases that have not traditionally been considered to involve leukocytes (such as osteoporosis or Alzheimer's disease).

The chemokines are a large family of signalling molecules with homology to interleukin-8, which have been implicated in regulating leukocyte trafficking both in physiological and pathological conditions. With more than fifty ligands and twenty receptors involved in chemokine signalling, the system has the requisite information density to address leukocytes through the complex immune regulatory processes from the bone marrow, to the periphery, then back through secondary lymphoid organs. However, this complexity of the chemokine system has at first hindered pharmacological approaches to modulating inflammatory responses through chemokine receptor blockade. It has proved difficult to determine which chemokine receptor(s) should be inhibited to produce therapeutic benefit in a given inflammatory disease.

More recently, a family of agents which block signalling by a wide range of chemokines simultaneously has been described: Reckless et al., Biochem J. (1999) 340:803-811. The first such agent, a peptide termed "Peptide 3", was found to inhibit leukocyte migration induced by 5 different chemokines, while leaving migration in response to other chemoattractants (such as fMLP or TGF-beta) unaltered. This peptide, and its analogs such as NR58-3.14.3 (i.e. Sequence ID No. 1 c(DCys-DGln-DIle-DTrp-DLys-DGln-DLys-DPro-DAsp-DLeu-DCys)-NH$_2$), are collectively termed "Broad Spectrum Chemokine Inhibitors" (BSCIs). Grainger et al., Biochem. Pharm. 65 (2003) 1027-1034 have subsequently shown BSCIs to have potentially useful anti-inflammatory activity in a range of animal models of diseases. Interestingly, simultaneous blockade of multiple chemokines is not apparently associated with acute or chronic toxicity, suggesting this approach may be a useful strategy for developing new anti-inflammatory medications with similar benefits to steroids but with reduced side-effects.

However, peptides and peptoid derivatives such as NR58-3.14.3, may not be optimal for use in vivo. They are quite expensive to synthesise and have relatively unfavourable pharmacokinetic and pharmacodynamic properties. For example, NR58-3.14.3 is not orally bioavailable and is cleared from blood plasma with a half-life period of less than 30 minutes after intravenous injection.

Two parallel strategies have been adopted to identify novel preparations that retain the anti-inflammatory properties of peptide 3 and NR58-3.14.3, but have improved characteristics for use as pharmaceuticals. Firstly, a series of peptide analogs have been developed, some of which have longer plasma half-lives than NR58-3.14.3 and which are considerably cheaper to synthesise. Secondly, a structure: activity analysis of the peptides has been carried out to identify pharmacophores in order to propose small non-peptidic structures which might retain the beneficial properties of the original peptide.

This second approach yielded several structurally distinct series of compounds that retained the anti-inflammatory properties of the peptides, including 16-amino and 16-aminoalkyl derivatives of the alkaloid yohimbine, as well as a range of N-substituted 3-aminoglutarimides. (Reference: Fox et al., J Med Chem 45 (2002) 360-370; WO 99/12968 and WO 00/42071). All of these compounds are broad-spectrum chemokine inhibitors which retain selectivity over non-chemokine chemoattractants, and a number of them have been shown to block acute inflammation in vivo.

The most potent and selective of these compounds was (S)-3-(undec-10-enoyl)-aminoglutarimide (NR58,4), which inhibited chemokine-induced migration in vitro with an $ED_{50}$ of 5 nM. However, further studies revealed that the aminoglutarimide ring was susceptible to enzymatic ring opening in serum. Consequently, for some applications (for example, where the inflammation under treatment is chronic, such as in autoimmune diseases) these compounds may not have optimal properties, and a more stable compound with similar anti-inflammatory properties may be superior.

As an approach to identifying such stable analogs, various derivatives of (S)-3-(undec-10-enoyl)-aminoglutarimide have been tested for their stability in serum. One such derivative, the 6-deoxo analog (S)-3-(undec-10-enoyl)-tetrahydropyridin-2-one, is completely stable in human serum for at least 7 days at 37° C., but has considerably reduced potency compared with the parental molecule.

One such family of stable, broad spectrum chemokine inhibitors (BSCIs) are the 3-amino caprolactams, with a seven-membered monolactam ring (see, for example, WO2005/053702 and WO2006/016152). However, further useful anti-inflammatory compounds have also been generated from other 3-aminolactams with different ring size (see for example WO2006/134385). Other modifications to the lactam ring, including introduction of heteroatoms and bicyclolactam ring systems, also yield compounds with BSCI activity (see, for example, WO2006/018609 and WO2006/085096).

To date, the identification of broad classes of agents with BSCI activity, and hence anti-inflammatory properties in vivo, has been based on optimising potency of the BSCI activity. For example, previous disclosures taught that introduction of 2,2-disubstitution (at the alpha- or key-carbon atom in the acyl side chain of acyl-3-aminolactams) leads to a considerable increase in potency as a BSCI, both in vitro and in vivo in models of acute inflammation, whether the 2,2-disubstituted acyl group was open chain (see WO2005/053702), monocyclic (see WO2006/134384) or polycyclic (see WO2006/016152).

However, potency of the desired pharmacological effect is only one factor in determining whether an agent will make a useful human pharmaceutical, albeit an important factor. In particular, the pharmacokinetics (or disposition of the agent within the body) exerts a major effect on the utility of a particular agent. Pharmacokinetics (defined in its broadest sense, as the study of the effects of the body on the drug, in contrast to pharmacodynamics, which is the study of the effects of the drug on the body) depends on a host of complex physiological processes, including (but not limited to) absorption, plasma stability, volume of distribution (and in particular rate of equilibration into 'target' tissues), metabolic transformation (including hepatic metabolism, such as cytochrome P450 isoenzyme mediated oxidation, and phase II metabolism such as sulfation and glucuronidation, and extrahepatic metabolism, such as serum enzymic modification), and excretion (such as renal clearance into urine and fecal elimination). These processes are often collectively referred to as the 'ADME' properties of the agent (ADME being an acronym for Absorption, Distribution, Metabolism and Excretion).

Another important factor in determining the utility of an agent as a human pharmaceutical is safety. Many, if not all, compounds administered elicit multiple effects on the body of which the desirable pharmacological effects are usually only a subset. The remaining effects may result in harm (toxic effects) or inconvenience (side-effects) to the patient. The study of such properties of candidate pharmaceutical agents is called toxicology or safety pharmacology. Unwanted effects can be broadly classified into two types. Class effects are intimately tied up with the desired pharmacological action, and (to a greater or less extent) are an inevitable consequence of manipulating the chosen molecular target. For example agents designed to prevent pathological inflammation may, to a degree, result in immunosuppression and an increased risk of infection. This is because inflammatory tissue damage and infection are both inextricably linked to the degree of immune system activity. As a result, all molecules sharing the identical pharmacological target will, to a greater or lesser extent, share class effects. In contrast, compound effects are specifically associated with a particular compound structure, usually as a result of an (often unexpected) interaction with a target distinct from the intended pharmacological target. In principle, it is possible to find another molecule with the same intended pharmacological effects but which is completely devoid of the compound-specific side-effects. Some compound effects are common (such as hERG interaction, which can result in dangerous prolongation of the QT interval during heart pacing, resulting potentially fatal cardiac arrythmias), while other compound effects may be apparently unique to the particular compound.

Crucially, despite decades of pharmaceutical development experience, there is still no generally accepted method for predicting either the ADME and pharmacokinetic properties of an agent, or its toxicology and safety pharmacology. It is for this reason that explicit testing, first using in vitro assay systems (such as hERG-expressing cell lines), then in animals and finally in phase I clinical trials in man, is a regulatory requirement worldwide for the development of a new pharmaceutical.

Methods have been described for predicting certain aspects of ADME from inspection of the molecular structure, and there can be little doubt that experienced medicinal chemists can reliably rule out many structures on purely theoretical grounds. An example of such a "rule of thumb" (for it is no more dependable than that) would be Lipinsky's "Rules of Five", based on the observation that most approved pharmaceuticals meet certain criteria related to molecular weight, number of rotatable bonds and polarity. Similarly, it is generally well known that molecules with large, hydrophobic groups are more likely to show an undesirable interaction with the hERG channel.

Such general guidelines, even when applied together, may be useful for eliminating unsuitable molecules but many very unsuitable molecules (for various reasons) would still slip though the net. Today, no-one would seriously countenance selecting a drug candidate from a class of active compounds on purely theoretical grounds. As a result, the discovery of a particular compound from within a class which has particularly advantageous ADME, pharmacokinetic, toxicological and safety pharmacological properties requires considerable practical experimentation among good candidates, and is a novel finding which could not be predicted even by those skilled in the art.

Here we describe the novel compound 3-(2',2'-dimethyl-propanoylamino)-tetrahydropyridin-2-one (I), which has not previously been reported.

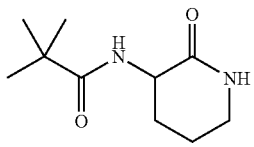

(I)

This compound is a specific member of the broad generic class of BSCIs which have been described previously (for example, see WO2006/134385). However, we now demonstrate that while all the molecules of the class have BSCI activity, compounds (I) has significantly superior properties for use as a human pharmaceutical as a result of its combination of ADME, pharmacokinetic, toxicology and safety pharmacology properties, when compared experimentally to other members of the class.

The carbon atom at position 3 of the lactam ring is asymmetric and consequently, the compounds according to the present invention have at least two possible individual forms, that is, the "R" and "S" configurations. The present invention encompasses the two enantiomeric forms and all combinations of these forms, including the racemic "RS" mixtures. With a view to simplicity, when no specific configuration is shown in the structural formula, it should be understood that the two individual enantiomeric forms and their mixtures are represented. Since enantiomeric inversion has no effect on the key ADME properties responsible for the superiority of the compound (and additionally has only a small effect on the potency of the compound as a BSCI), both enantiomeric forms, as well as their admixtures, represent specific examples which are materially superior to the class in general.

Preferably, the compound of formula (I) according to this invention will be the compound of formula (I').

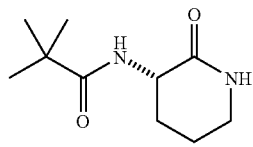

(I')

The compound (I'), having the (S)-configuration at the stereocentre, is 5-25 fold more potent as a BSCI than the (R)-enantiomer.

Also provided are pharmaceutical compositions, comprising, as active ingredient, a compound of general formula (I) or (I'), or a pharmaceutically acceptable salt thereof, and at least one pharmaceutically acceptable excipient and/or carrier.

By pharmaceutically acceptable salt is meant in particular the addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33:201-217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax. Other appropriate pharmaceutically acceptable excipients and/or carriers will be known to those skilled in the art.

The pharmaceutical compositions according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The invention also provides the use of a compound of formula (I) or (I'), or a pharmaceutically acceptable salt thereof, for the preparation of a medicament intended to treat inflammatory disorder.

The invention includes compounds, compositions and uses thereof as defined, wherein the compound is in hydrated or solvated form.

In comparison to the prior art the improvement of the present invention lies in the unexpected observation that 3-(2',2'-dimethylpropanoylamino)-tetrahydropyridin-2-one has superior ADME properties compared to the general classes of lactam BSCIs which have been described previously (such as, for example, the International applications supra). Although such compounds were reported as having acceptable pharmacodynamic properties (that is, they have a potent anti-inflammatory effect in vivo as a result of their BSCI activity), and it was inferred that they must have acceptable pharmacokinetic, and hence ADME, properties, nevertheless direct assessment of the ADME properties suggest that 3-(2',2'-dimethylpropanoylamino)-tetrahydropyridin-2-one is notably and unexpectedly superior (see the examples below).

In particular, while previous in vitro stability studies in serum suggested that lactam BSCIs were considerably better than the earlier imide BSCIs (see, for example, WO99/12968), as reported in the literature (for example Fox et al. *J. Med. Chem.* 2005 48:867-74), it is now clear that many (or indeed most) of the lactam class of BSCIs are subject to unwanted metabolism in vivo. We have made and tested more than a dozen BSCIs of the acylaminolactam class, and with the exception of 3-(2',2'-dimethylpropanoylamino)-tetrahydropyridin-2-one, all of the lactam class BSCIs tested to date are subject to rapid liver metabolism (either cytochrome P450 mediated hydroxylation and/or phase II metabolism).

At least partly as a consequence of the reduced in vivo metabolism, the overall clearance of 3-(2',2'-dimethylpropanoylamino)-tetrahydropyridin-2-one is markedly lower than for the other lactam BSCIs tested. As a result, the exposure following a single oral dose is more than 10-fold higher for 3-(2',2'-dimethylpropanoylamino)-tetrahydropyridin-2-one. 3-(2',2'-dimethylpropanoylamino)-tetrahydropyridin-2-one is therefore more suitable for use as a human pharmaceutical, particularly where chronic oral exposure is required for efficacy, than most (if not all) of the lactam BSCIs previously disclosed.

Prior art peptides (such as NR58-3.14.3) have the disadvantages that: (a) they are expensive and require solid phase synthesis (at least for the longer ones) and (b) they clear very quickly via the kidneys and (c) they are generally very much less potent (>25 fold less potent in vitro and >10,000 fold less potent in vivo).

The prior art aminoglutarimides are cheap, not cleared quickly via the kidneys and more potent in vitro BUT they are extremely unstable in serum (as a result of an enzymatic opening of the imide ring; see, for example, Fox et al. *J. Med. Chem.* 2005 48:867-74). As a result aminoglutarimide BSCIs, such as (S)-3-(undec-10-enoylamino)glutarimide, are at least 250-fold less potent in vivo than 2',2'-dimethylpropanoylamino)-tetrahydropyridin-2-one, even in models of acute inflammation (such as LPS-induced endotoxemia marked by systemic TNF-α production, where the impact of compound stability and ADME properties is least apparent).

Another series of structurally related (but functionally largely dissimilar) compounds which have been described in the literature are bacterial autoinducer compounds typically based around the 6-membered homoserinelactone structure, usually with a 3-oxo-acyl side chain (for example, see Bycroft et al. U.S. Pat. No. 5,969,158 which claims a broad range of such compounds). Interestingly, although such disclosures include generic formulae that encompass lactams as well as lactones, few if any of the exemplified compounds with bacterial autoinducer properties have lactam headgroups. All such compounds (but particularly those with a lactone headgroup and/or a 3-oxoacyl tail group) are known to be relatively unstable limiting their applications as medicaments.

The improvement described here, 3-(2',2'-dimethylpropanoylamino)-tetrahydropyridin-2-one, is cheap to synthesise (and the method disclosed here allows straightforward synthesis even on a Kg scale), and shows excellent metabolic stability not only in isolated serum in vitro (a property shared with the whole lactam class of BSCIs disclosed previously) but also in vivo. As a result, the compounds of the present invention is (among those compounds studied extensively to date) uniquely optimised for the treatment of inflammatory diseases in man in terms of efficacy, potency and pharmaceutical properties such as ADME, pharmacokinetics, toxicology and safety pharmacology.

According to this invention, inflammatory disorders intended to be prevented or treated by the compounds of formula (I) or (I') or the pharmaceutically acceptable salts thereof or pharmaceutical compositions or medicaments containing them as active ingredients include notably:

autoimmune diseases, for example such as multiple sclerosis, rheumatoid arthritis, lupus, irritable bowel syndrome, Crohn's disease;

vascular disorders including stroke, coronary artery diseases, myocardial infarction, unstable angina pectoris, atherosclerosis or vasculitis, e.g., Behcet's syndrome, giant cell arteritis, polymyalgia rheumatica, Wegener's granulomatosis, Churg-Strauss syndrome vasculitis, Henoch-Schönlein purpura and Kawasaki disease;

viral infection or replication, e.g. infections due to or replication of viruses including pox virus, herpes virus (e.g., Herpesvirus samiri), cytomegalovirus (CMV), hepatitis viruses or lentiviruses (including HIV);

asthma, and related respiratory disorders such as allergic rhinitis and COPD;

osteoporosis; (low bone mineral density);

tumor growth;

organ transplant rejection and/or delayed graft or organ function, e.g. in renal transplant patients;

a disorder characterised by an elevated TNF-α level;

psoriasis;

skin wounds and other fibrotic disorders including hypertrophic scarring (keloid formation), adhesion formations following general or gynaecological surgery, lung fibrosis, liver fibrosis (including alcoholic liver disease)

or kidney fibrosis, whether idiopathic or as a consequence of an underlying disease such as diabetes (diabetic nephropathy);

disorders caused by intracellular parasites such as malaria or tuberculosis;

neuropathic pain (such as post-operative phantom limb pain, post-herpatic neuralgia etc)

allergies; or

Alzheimer's disease.

According to this invention, further inflammatory disorders include:

ALS;

antigen induced recall response immune response suppression.

These clinical indications fall under the general definition of inflammatory disorders or disorders characterized by elevated TNFα levels.

It should be noted, for the avoidance of doubt, that the primary mechanism of action of the BSCIs, including the compounds claimed herein, is on the immune system. Consequently, the claimed beneficial effects on diseases such as viral infection and/or replication and tumour growth (conditions which, of themselves, are not primarily diseases of the immune system) results from the consequential effects of modulating the immune system on the infection and/or replication patterns of the virus, or on the growth and spread of the tumour. Since BSCIs, including the compounds claimed herein, do not (in general) directly affect viral replication or tumour growth, they would be expected to have no effect at all in an isolated system (for example, in an in vitro infection of a cultured cell line, or in a tumour cell line proliferation assay) where an intact and functioning immune system is absent. Consequently, prior information relating to the effects of any compounds in such isolated systems cannot inform the development of BSCIs, which act on the immune system.

Where legally permissible, the invention also provides a method of treatment, amelioration or prophylaxis of the symptoms of an inflammatory disease (including an adverse inflammatory reaction to any agent) by the administration to a patient of an anti-inflammatory amount of a compound, composition or medicament as claimed herein.

Administration of a medicament according to the invention can be carried out by topical, oral, parenteral route, by intramuscular injection, etc.

The administration dose envisaged for a medicament according to the invention is comprised between 0.1 mg and 10 g depending on the formulation and route of administration used.

According to the invention, the compounds of general formula (I) or (I') can be prepared using the processes described hereafter.

Preparation of the Compounds of General Formula (I) or (I')

All the compounds of general formula (I) or (I') can be prepared easily according to general methods known to the person skilled in the art.

Compound (I) is a colourless crystalline compound that can be made from ornithine and 2,2-dimethylpropionyl chloride. For the synthesis of (I') enantiomerically pure (S)-ornithine would be used. A ring closure starting with either ornithine or its methyl ester is possible. The amino acid can be esterified in dry methanol by in situ generation of HCl using trimethylsilyl chloride. Alternatively, isolated ester can be ring closed, in either case using triethylamine. The crude product can then be acylated after a solvent exchange.

The acylaminolactam product (I) has significant water solubility and as a result, the acylation conditions used for related, more hydrophobic, products (see, for example, WO2006/134385) were unsatisfactory. The use of three equivalents of sodium carbonate as base resulted in the formation of significant precipitation of sodium hydrogen carbonate by-product unless a large amount of water was used (>4 mL/mmol ornithine). At these concentrations the extraction of the product into dichloromethane is not efficient. Therefore the three equivalents of sodium carbonate were replaced with 2.5 equivalents of potassium hydroxide (which neutralises the 2.5 equivalents of triethylamine hydrochloride generated in the ring closure step). With this base significantly less water can be used (less than 1 mL/mmol ornithine) (final pH 8-9). Extraction of the aqueous layer with EtOAc (3×2 mL/mmol ornithine) and recrystallisation from EtOAc (0.5 mL/mmol, hot) and 40-60 petroleum (5 mL/mmol) produced a first crop in 43% yield (4.25 g from 50 mmol ornithine).

Note that if the pH of the aqueous layer is too low during the work-up then small quantities of triethylamine hydrochloride will be extracted into the EtOAc layer. Attempts at washing this EtOAc solution with water will extract significant quantities of the lactam product (I) along with the amine hydrochloride. This can be avoided by raising the pH of the aqueous layer to 12 (for example by addition of roughly one equivalent of KOH with respect to acid chloride) before the EtOAc extraction is attempted, then only triethylamine free base is extracted along with the lactam product (I), which can be removed more easily by evaporation or during recrystallisation.

The following preferred synthetic route is therefore provided:

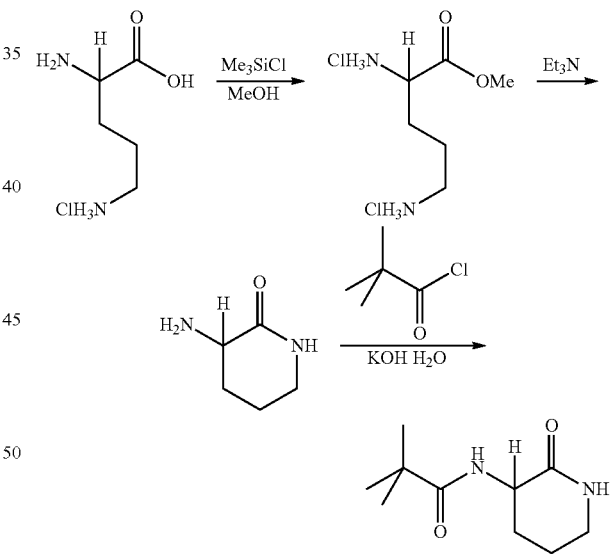

(S)-Ornithine monohydrochloride (50 mmol) is suspended in dry methanol (100 ml) and trimethylsilyl chloride (75 mmol) added. The reaction is heated at reflux for 24 hours. Triethylamine (150 mmol) is then added and the reaction is heated at reflux for 48 hours. The methanol is then removed under reduced pressure (optionally, toluene may be added in the latter stages to facilitate removal), and the residue is dissolved in water (20 mL), with KOH (125 mmol) added.

The mixture is cooled to 0° C. then 2,2-Dimethylpropionyl chloride (50 mmol) is added slowly and the reaction stirred for 18 hours, while warming to ambient temperature. Solid KOH (50 mmol) is then added and once it has dissolved the reaction is extracted with EtOAc (3×100 mL). The combined organic layers are quickly dried over a combination of $K_2CO_3$ and $Na_2SO_4$, and reduced under low pressure. The solid residue is then recrystallised from EtOAc (25 mL)/40-60 petroleum ether (200-250 mL) to give the lactam (I') as a crystalline solid (greater than 50% yield).

The identity and purity (>95%) of the product was then confirmed by proton NMR spectroscopy OH (400 MHz, $CDCl_3$) 6.63 (1H, br s, NH), 6.01 (1H, br s, NH), 4.20 (1H, dt, J 11, 5.5, CHNH), 3.40-3.31 (2H, m, $CH_2NH$), 2.61 (1H, dq, J 13, 4.5, $CH_2$), 1.97-1.88 (2H, m, $CH_2$), 1.50 (1H, dddd, J 13, 12, 9.5, 7.5, $CH_2$), 1.22 (9H, s, 3×$CH_3$).

DEFINITIONS

The term "about" refers to an interval around the considered value. As used in this patent application, "about X" means an interval from X minus 10% of X to X plus 10% of X, and preferably an interval from X minus 5% of X to X plus 5% of X.

The use of a numerical range in this description is intended unambiguously to include within the scope of the invention all individual integers within the range and all the combinations of upper and lower limit numbers within the broadest scope of the given range. Hence, for example, the range of 0.1 mg to 10 g specified in respect of (inter alia) the dose of 3-(2',2'-dimethylpropanoylamino)-tetrahydropyridin-2-one to be used is intended to include all doses between 0.1 mg and 10 g and all sub-ranges of each combination of upper and lower numbers, whether exemplified explicitly or not.

As used herein, the term "comprising" is to be read as meaning both comprising and consisting of: Consequently, where the invention relates to a "pharmaceutical composition comprising as active ingredient" a compound, this terminology is intended to cover both compositions in which other active ingredients may be present and also compositions which consist only of one active ingredient as defined.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference (where legally permissible).

The following examples are presented in order to illustrate the above procedures and should in no way be considered to limit the scope of the invention.

FIGURES

FIG. 1 (panels A to E) shows the time-concentration graphs for the five compounds (I') to (V) tested, following administration of a single 3 mg/kg dose in 1% CMC via the oral route to rats. The three lines for each compound represent three replicate animals. The Y-axis represents concentration in units of ng/ml (0-3000); the X-axis represents time in units of minutes (0-480).

Figure 2:
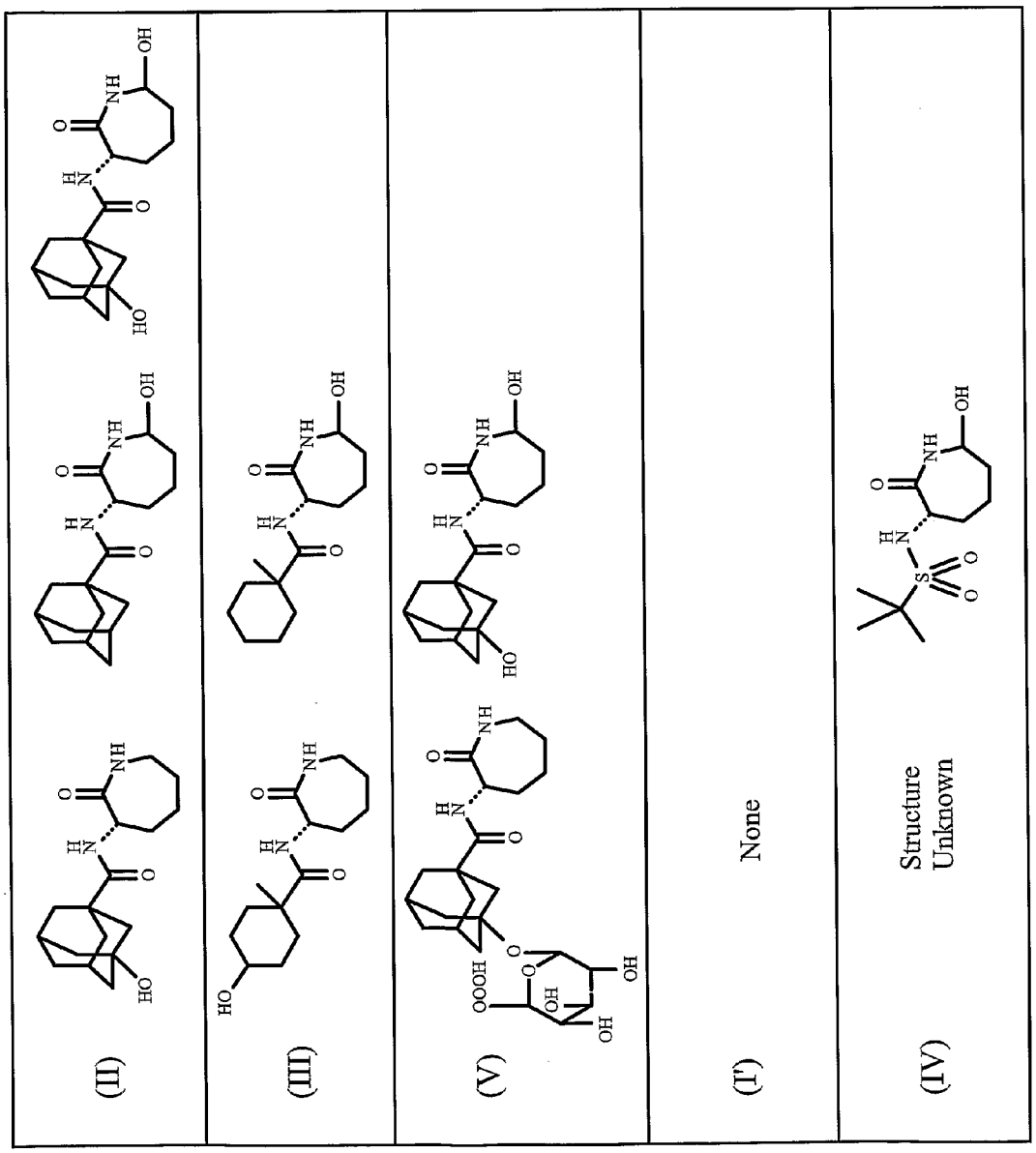
Figure 3A:
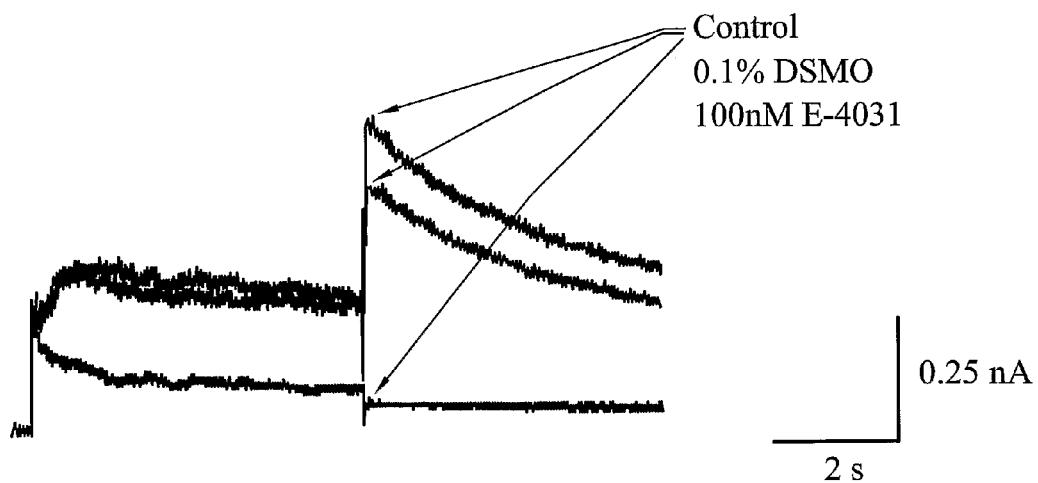
Figure 3B:
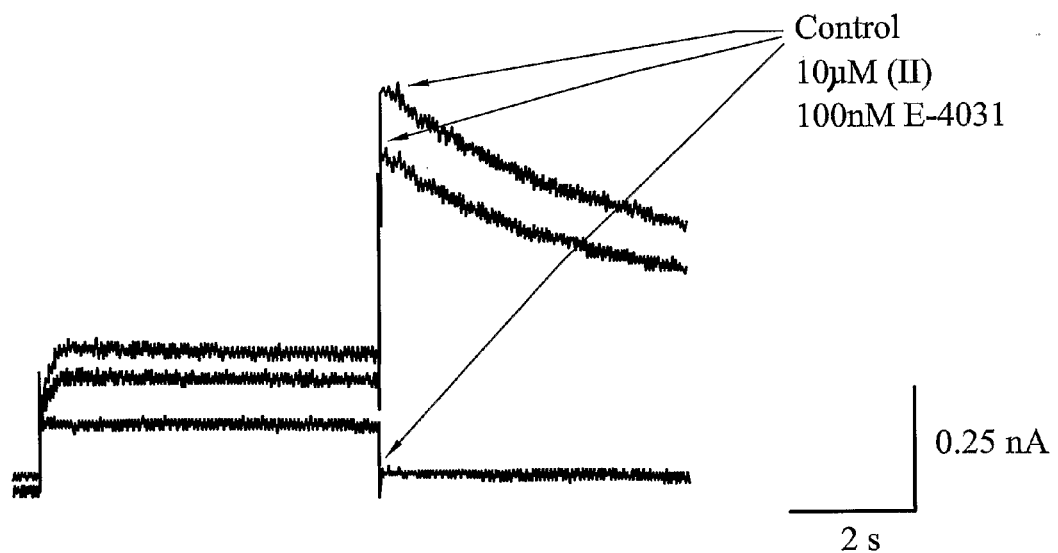
Figure 3C:
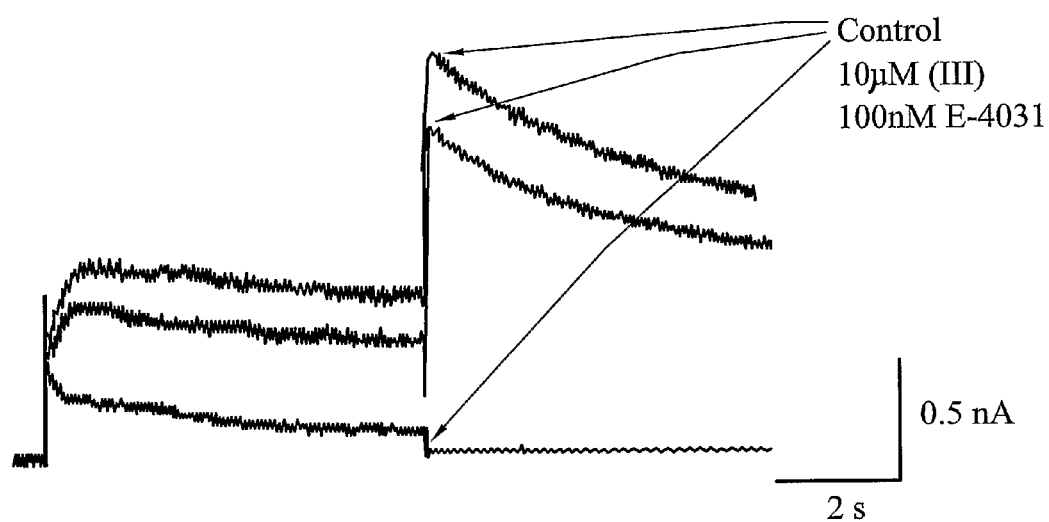
Figure 3D:
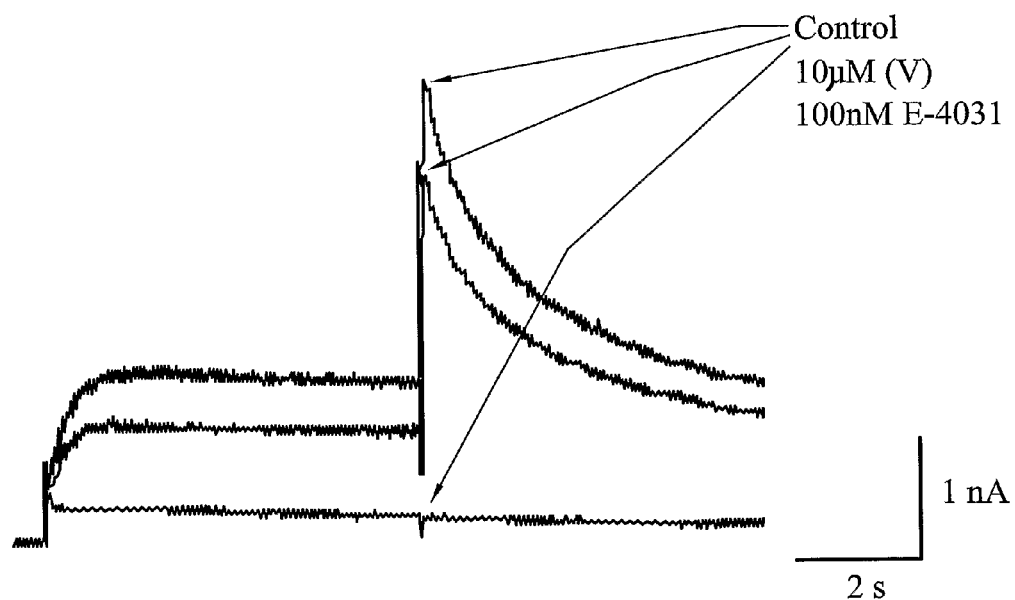
Figure 3E:
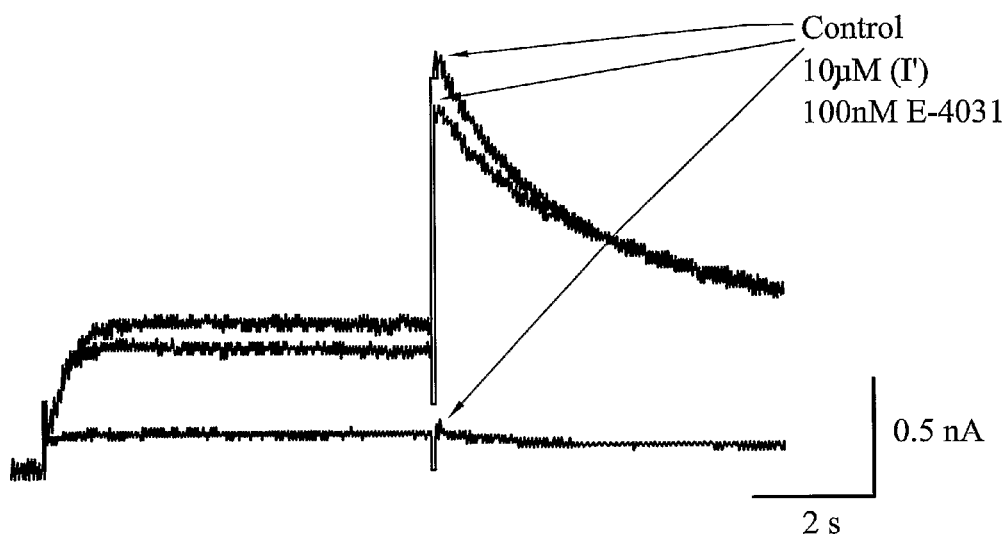
Figure 3F:
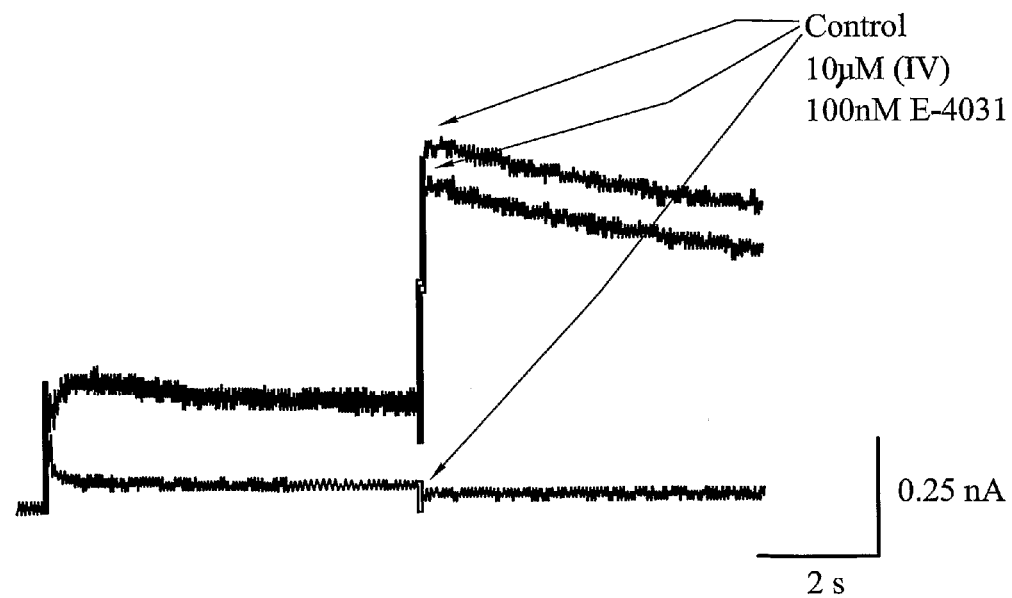
Figure 3G:
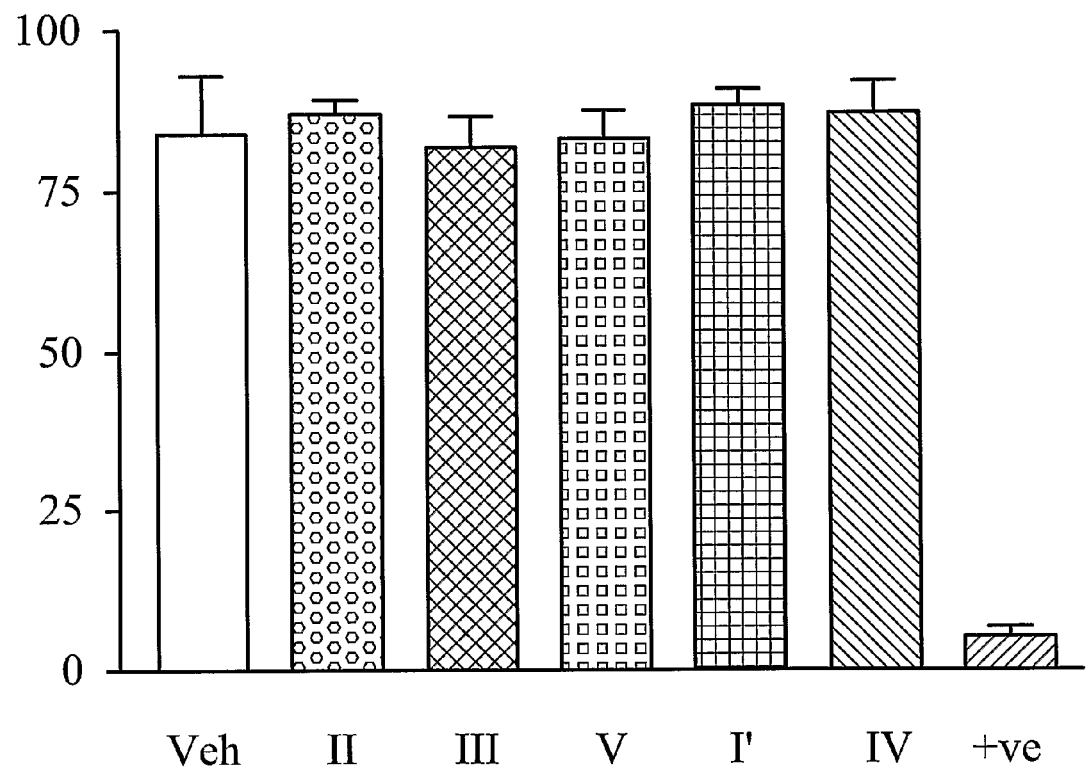

FIG. 2 shows the major metabolites identified by LC-MS-MS (in full scan mode) on pooled urine collected over 24 hrs from rats exposed to a single oral dose of each of the five compounds (I') to (V) tested, administered in 1% CMC at 3 mg/kg. Note that a major metabolite of compound (IV) has been identified but its structure was not elucidated by comparison of fragmentation/re-arrangement patterns in the publicly available Metabolite ID databases. Although the concentrations of the individual metabolites were not determined, they are shown in qualitative order of abundance in urine, with the most abundant species on the left of each row.

FIG. 3 (panels A-F) shows the current versus time graphs for cells expressing the hERG gene product, when exposed to either vehicle or to the five compounds (I') to (V), each in a separate experiment. In each experiment, replicate cells were exposed to the positive control compound, which completely blocks hERG-transduced current. The Y-axis represents current in units of nA; the X-axis represents time in units of seconds. Panel G shows the hERG tailcurrent (the area under the time versus current graphs in panels A-F) for replicate cells exposed to each compound or to 0.1% DMSO vehicle alone (Veh) or to the positive control compound E-4031 (+ve). The Y-axis of the histogram in panel G represents percentage inhibition of the hERG tail current relative to untreated cells.

Figure 4:
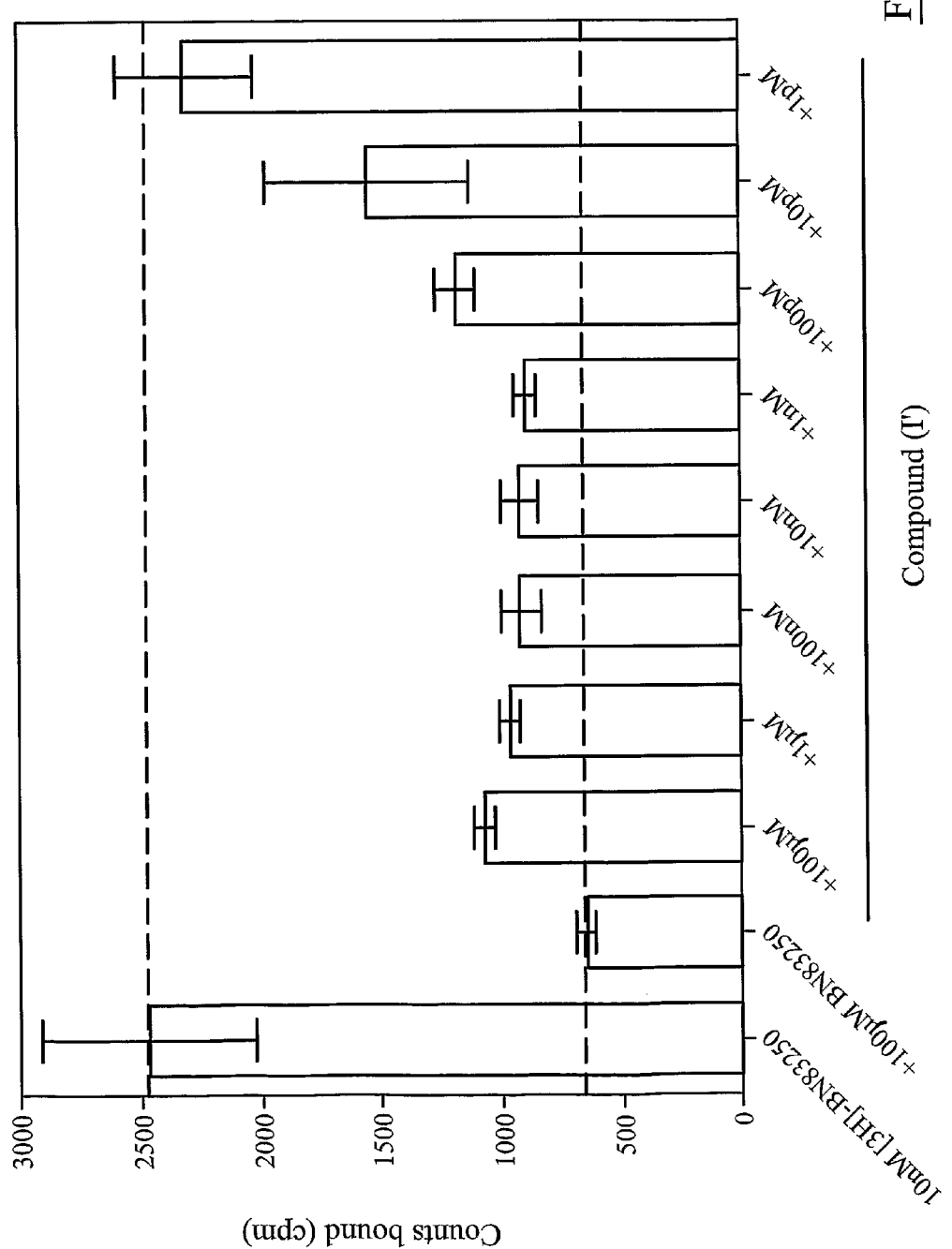
Figure 5A:
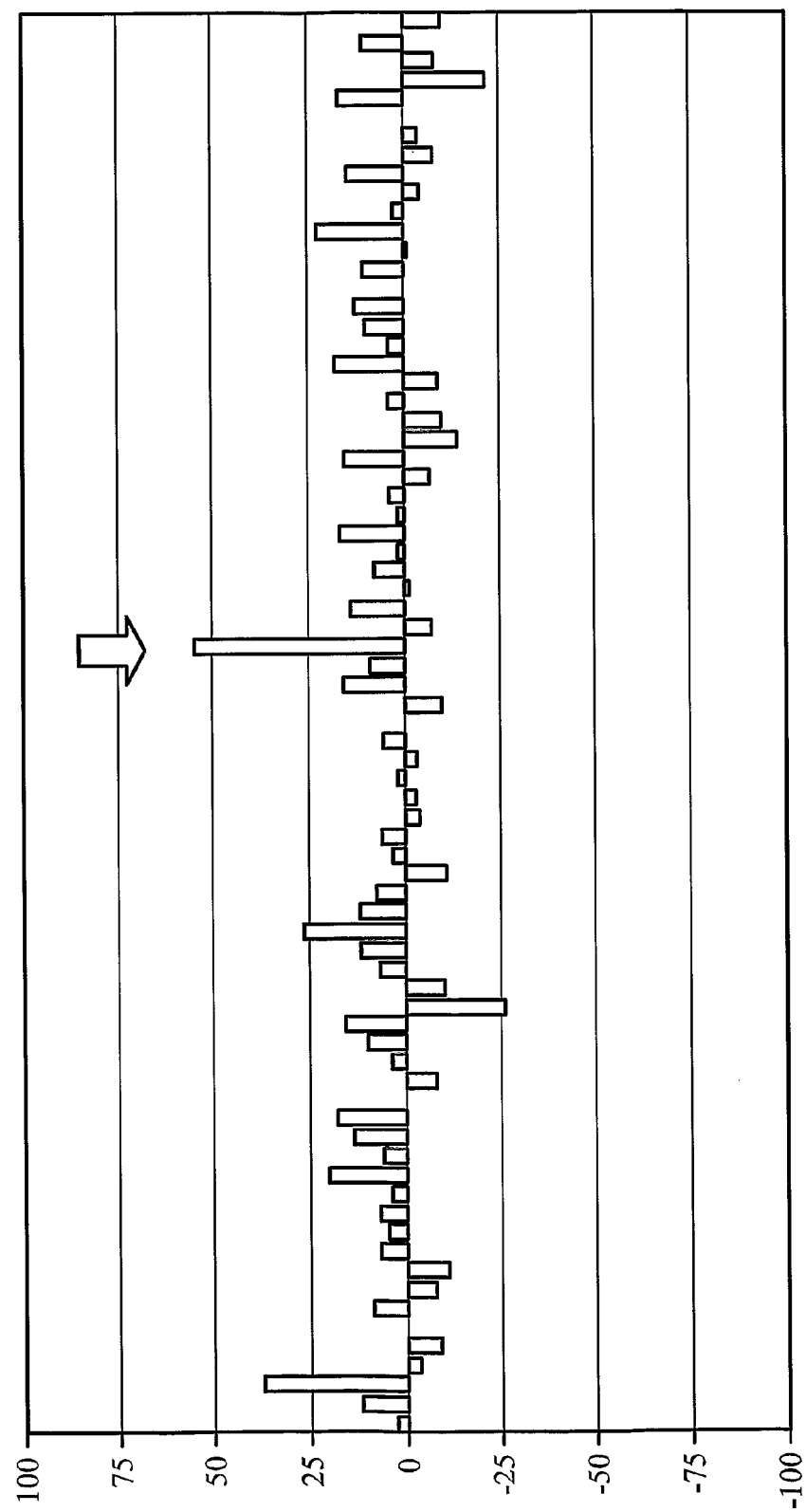
Figure 5B:
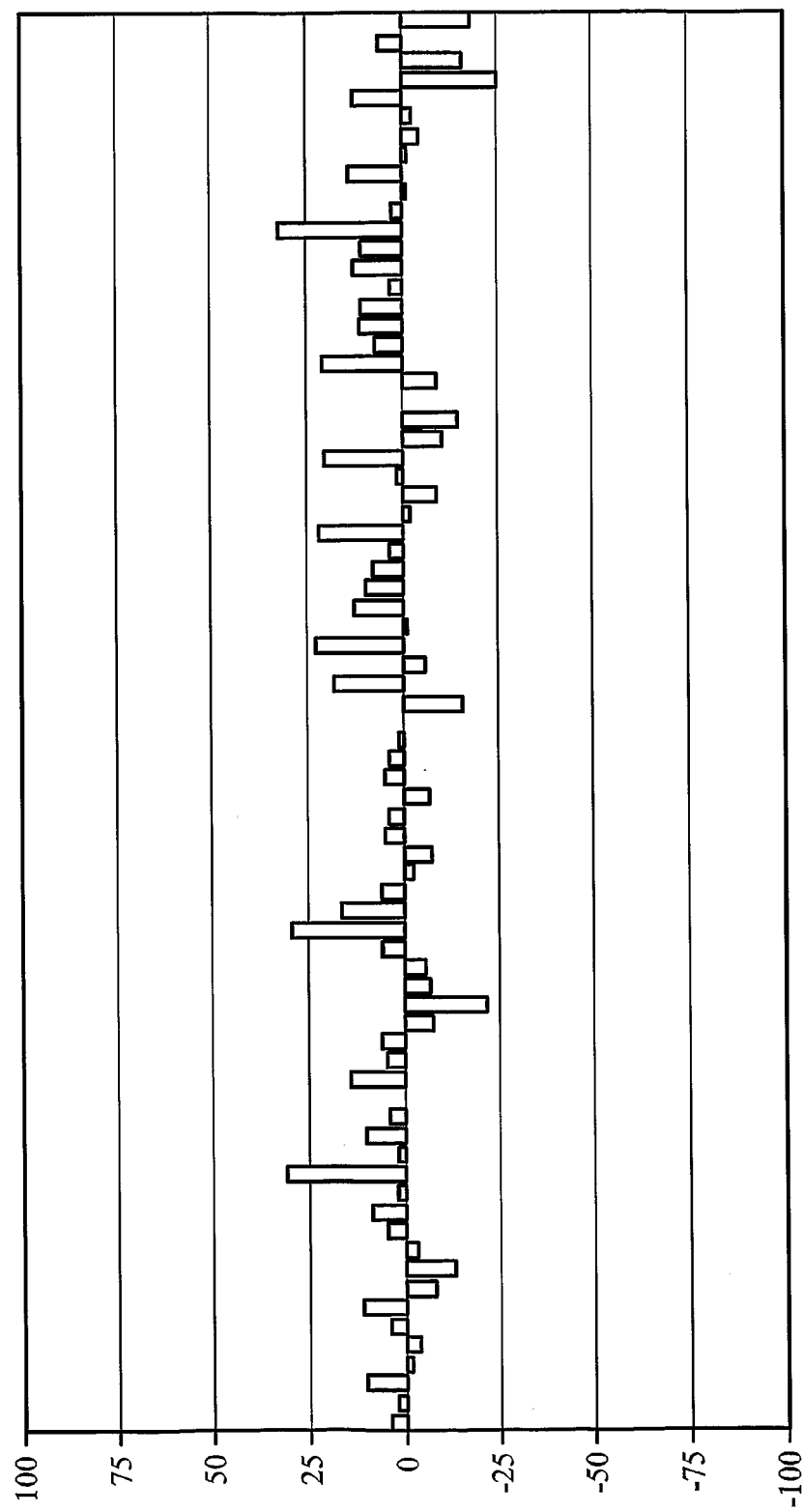
Figure 5C:
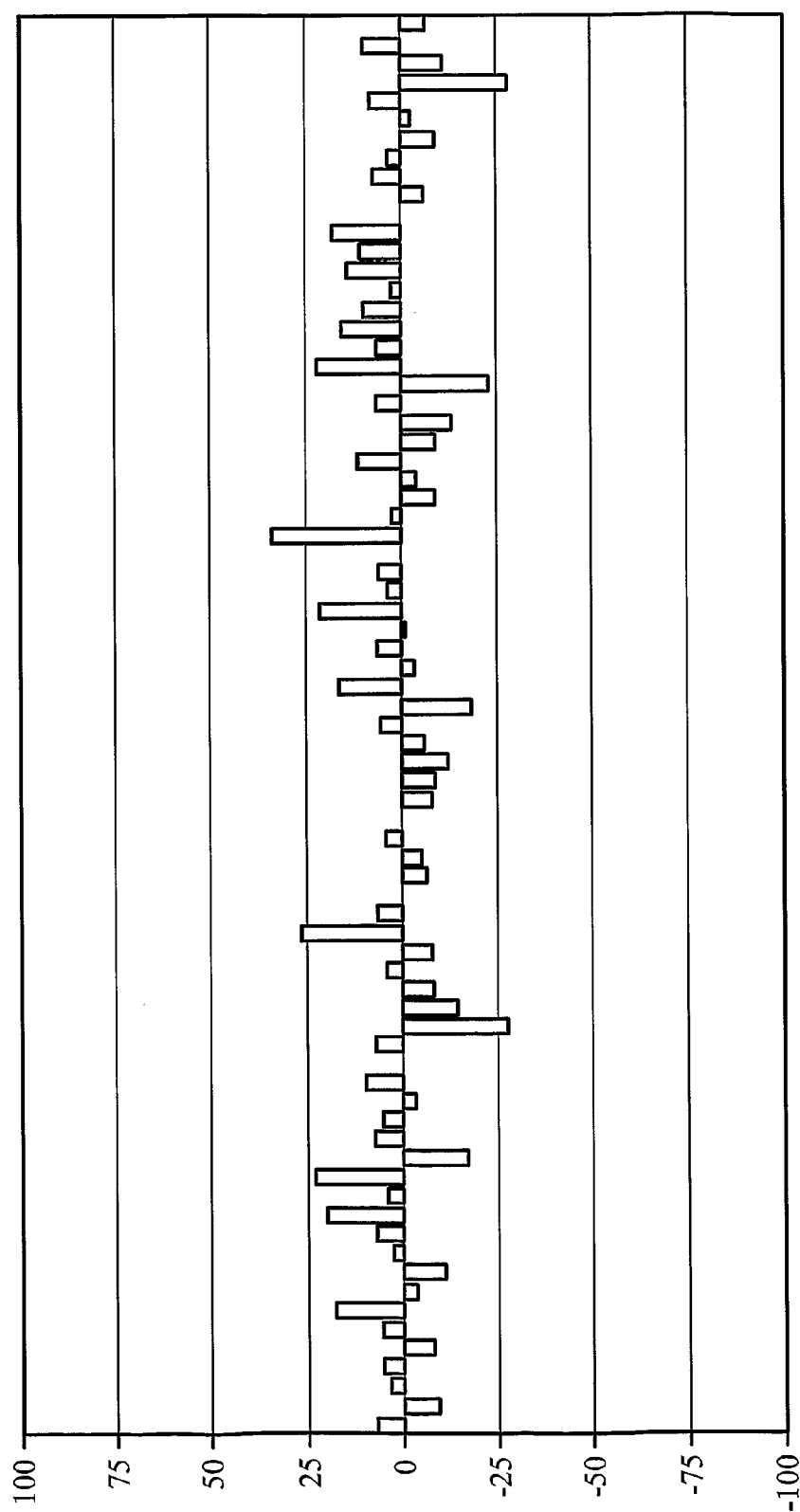
Figure 5D:
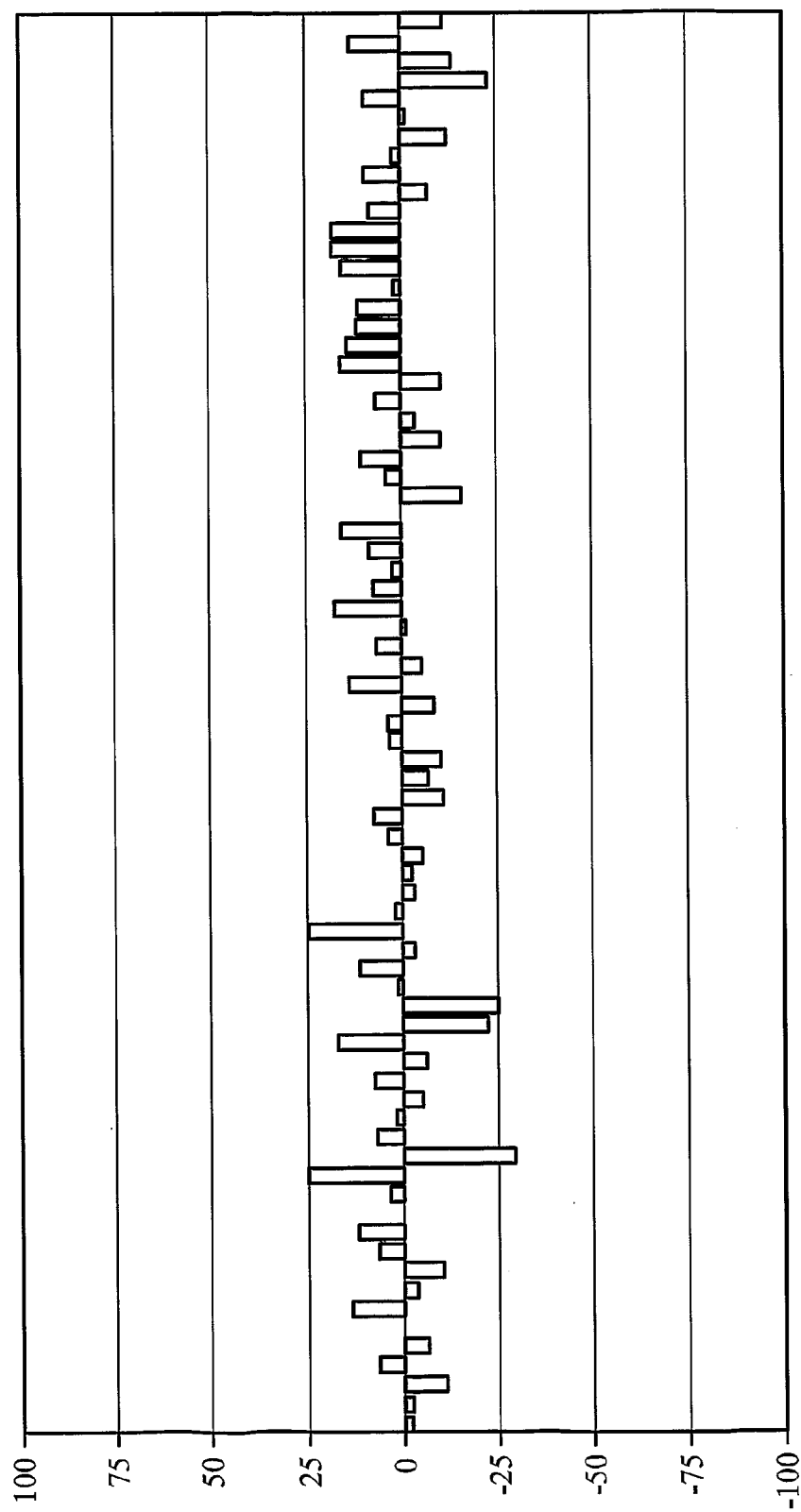
Figure 5E:
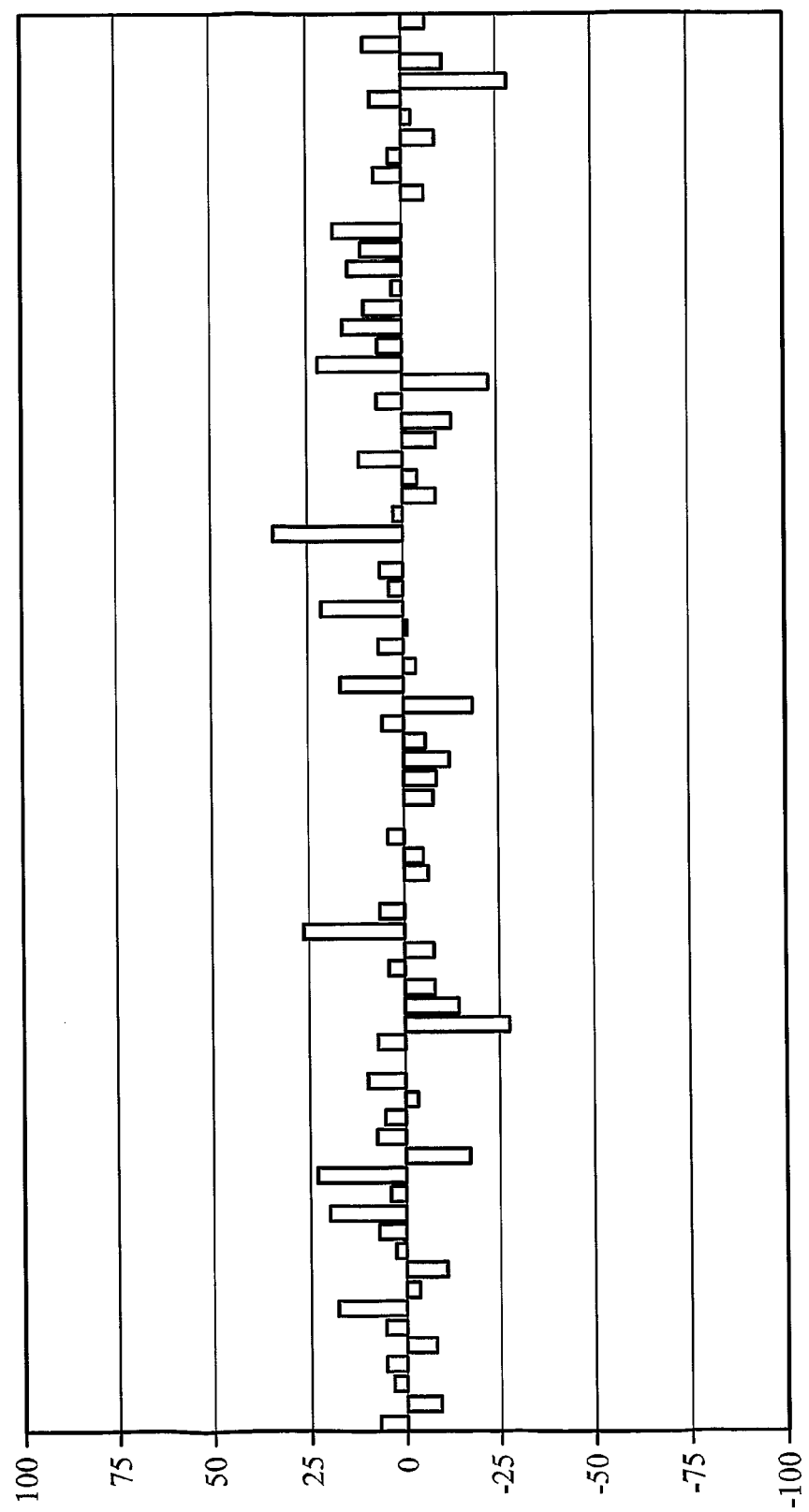
Figure 6A:
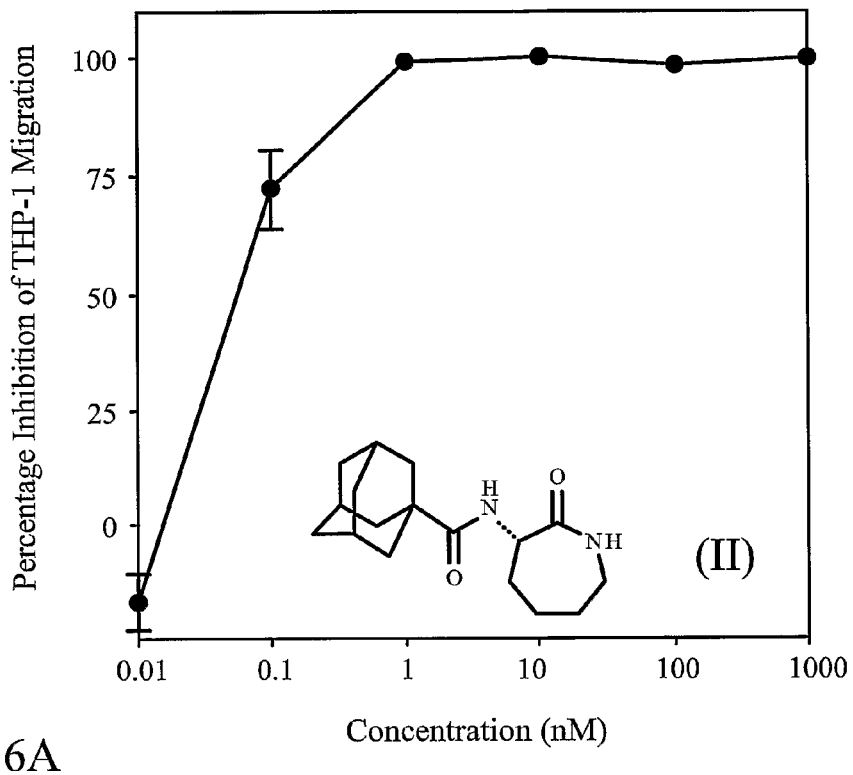
Figure 6B:
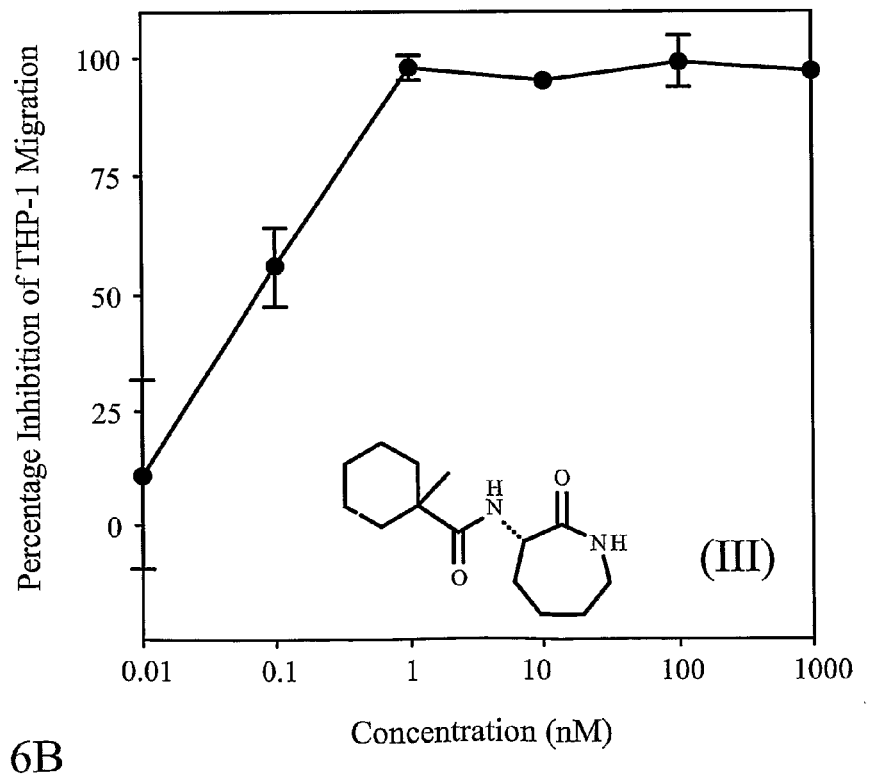
Figure 6C:
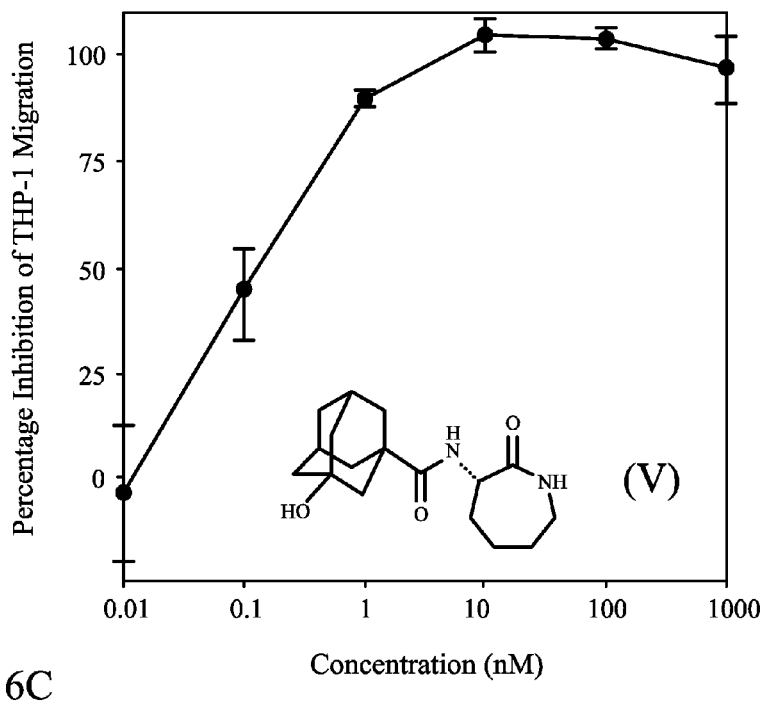
Figure 6D:
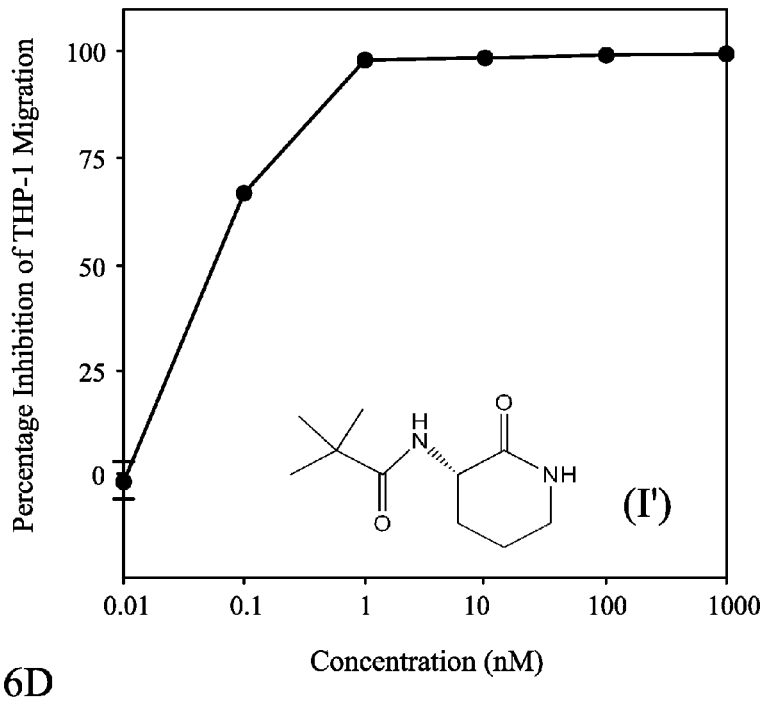
Figure 6E:
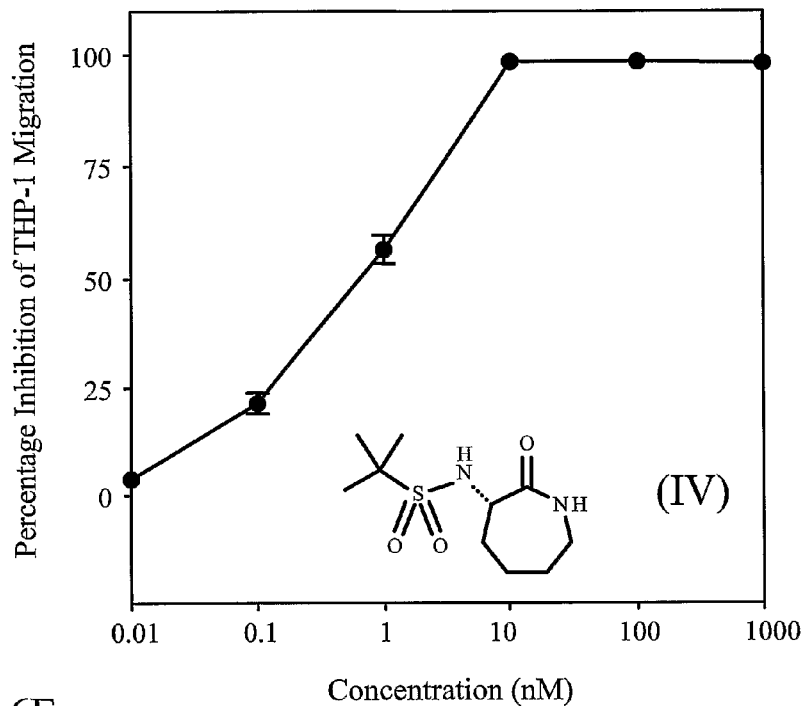
Figure 7A:
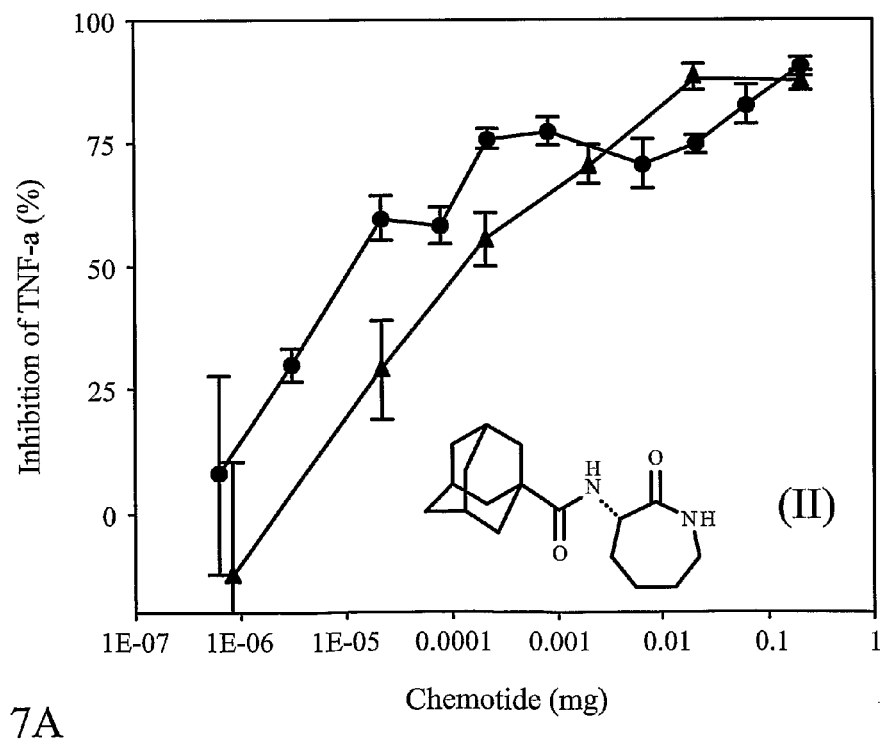
Figure 7B:
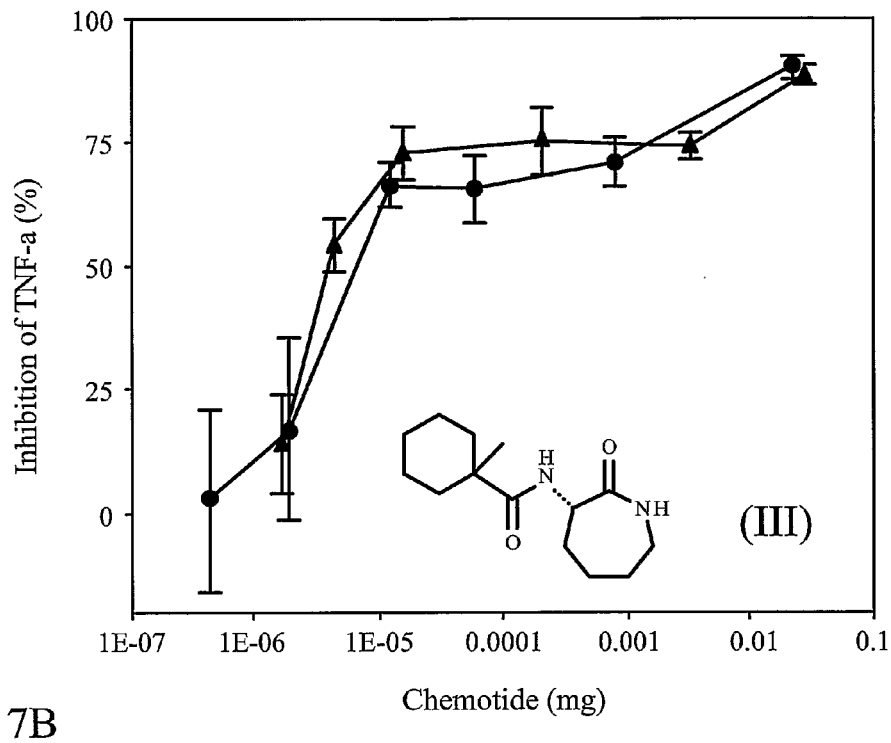
Figure 7C:
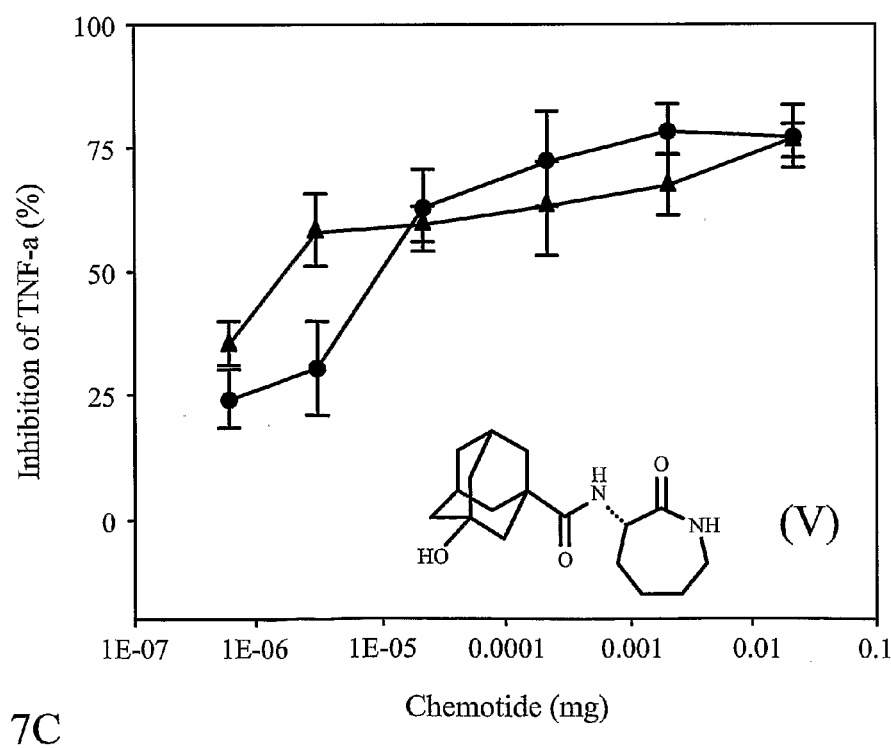
Figure 7D:
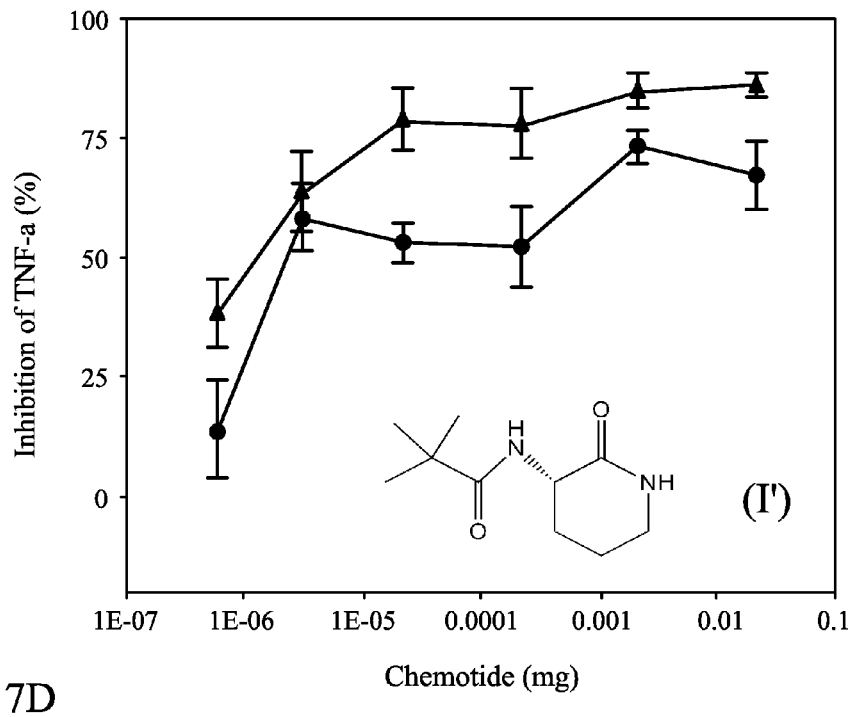
Figure 7E:
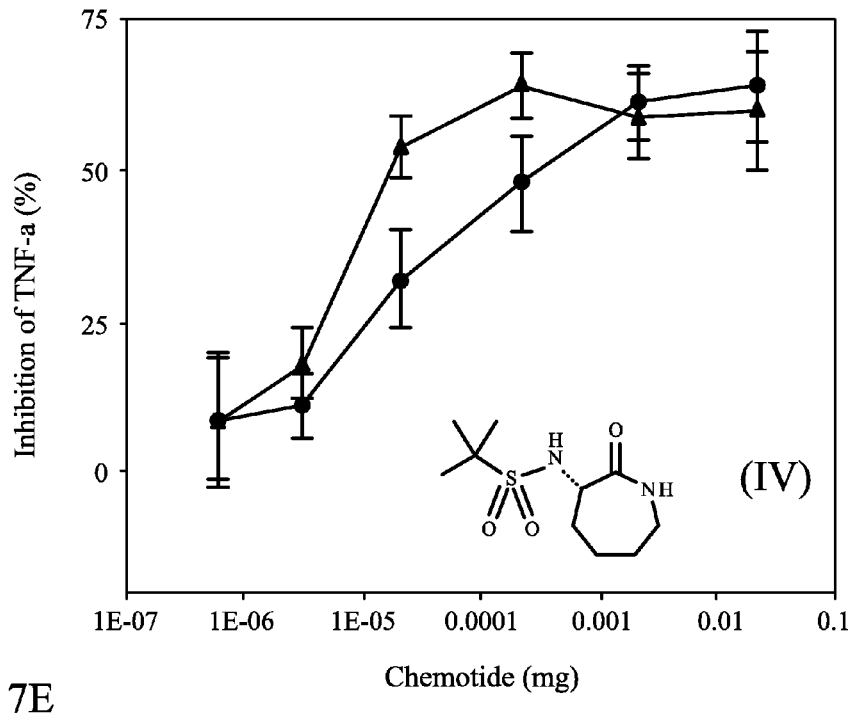

FIG. 4 shows a typical binding curve for compound (I'). In this experiment, each reaction received 10 nM labelled BN83250 (a lactam BSCI which binds to the same receptor as compound (I')), together with various competitors (100 μM-1 pM). The total specific binding was the amount displaced by a large excess (100 μM). Each bar represents the mean of three replicate determinations, with whiskers representing SEM. The Y-axis represents the radioactive counts bound in each experiments in units of counts per minute (cpm). The upper dashed line represents the total binding under the conditions of the experiment, while the lower dashed line represents the non-specific binding; the specific binding is represented by the distance between the dashed lines.

FIG. 5 shows the profile of cross-reactivity for each of the five compounds (I') to (V) (panel A: (II); B: (III); C: (V); D: (I') and E: (IV)) against a panel of 75 different receptors that compose the CEREP panel (see text). The compounds were tested at a single concentration (10 μM), and the inhibition of binding (Y-axis of each histogram) for a known ligand to each of the 75 receptors is reported (−100% therefore represents a 2-fold increase in binding of the specific ligand in the presence of the test compound). All reactions were performed in duplicate, and the bars represent the mean (no estimate of the replicate error is shown to simplify the graphs). Only a 50% or greater inhibition (or stimulation) of binding (representing an ED50 below 10 μM for the interaction of the test compound with the particular receptor) was considered statistically and biologically significant in this screening assay. For the five compounds tested here, only one interaction (that of compound (II) with the NK2 receptor, marked by the arrowhead in panel A) was considered potentially significant, although even this interaction was weak (estimated ED50 5-10 μM).

FIG. 6 (panels A-E) shows representative dose response curves for the inhibition of chemokine-induced leukocyte migration in vitro, for each of the five compounds (I') to (V) in the ChemoTx™ transwell migration assay. In each experiment, THP-1 cells were induced to migrate using a maximally effective dose of the chemokine MCP-1 in the presence or absence of various doses (from 10 μM to 1 μM) of each compound. An appropriate vehicle control was used in each experiment. The percentage inhibition of MCP-1 induced migration (calculated as the number of cells migrated in the presence of MCP-1 minus the number of cells migrated with MCP-1 omitted from the lower chamber) at each concentration of each test compound is shown as the mean of triplicate determinations, with whiskers representing SEM. The ED50 was estimated by linear interpolation of the presented graphs. The Y-axis of each graph represents the percentage inhibition of MCP-1 induced migration; the X-axis represents the concentration of test compound present in units of nM (0.01-1000).

FIG. 7 shows representative dose response curves for the inhibition of LPS induced TNF-α production in vivo in a murine model of sub-lethal endotoxemia. In each experiment, groups of six mice received pre-treatment with the five compounds (panel A: (II); B: (III); C: (V); D: (I') and E: (IV)) at various doses, via either the oral route (circles) or subcutaneous route (triangles). 30-60 mins later, animals were challenged with LPS via the intraperitoneal route, and serum was prepared from a terminal bleed 3 hours later. The level of TNF-α in the blood was measured by ELISA, and the degree of inhibition of LPS-induced TNF-α production (calculated as the concentration of TNF-α in mice exposed to LPS minus the concentration of TNF-α in mice which received a sham exposure to endotoxin-free PBS) is shown on the Y-axis of each graph as the mean of six animals, with whiskers representing SEMs. The concentration of TNF-α in mice receiving LPS but no BSCI treatment was typically 5,000 to 6,000 pg/ml on average (compared to <10 pg/ml in unchallenged mice). The ED50 was estimated by linear interpolation of the presented graphs. The X-axis of each graph represents the dose of each compound administered to each mouse in the group in units of mg (1E-07 to 1).

Figure 8:
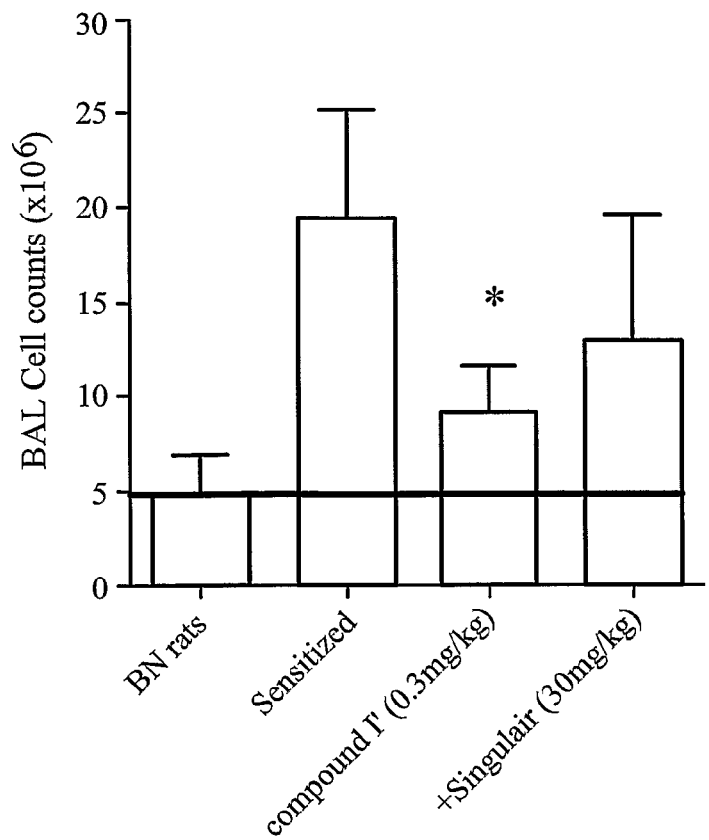

FIG. 8 shows the effect of compound (I') on lung inflammation in a representative experiment, as assessed by cell counts in BAL fluid in a rodent model of asthma. Bars represent mean cell counts, shown on the Y axis in units of $10^6$ cells, for groups of 5 animals with whiskers representing SEM; *$p<0.01$ versus 'sensitised' using Student's unpaired t-test assuming equal variance, with two tails). The horizontal line represents the average number of leukocytes present in BAL fluid from the lungs of unchallenged rats. All rats in the remaining three groups received the same sensitisation and challenge regimen, but were either treated with vehicle only ('Sensitised'), or with compound (I') at 0.3 mg/kg bodyweight or with monteleukast ('Singulair™') at 30 mg/kg bodyweight, all administered daily by oral gavage.

Figure 9:
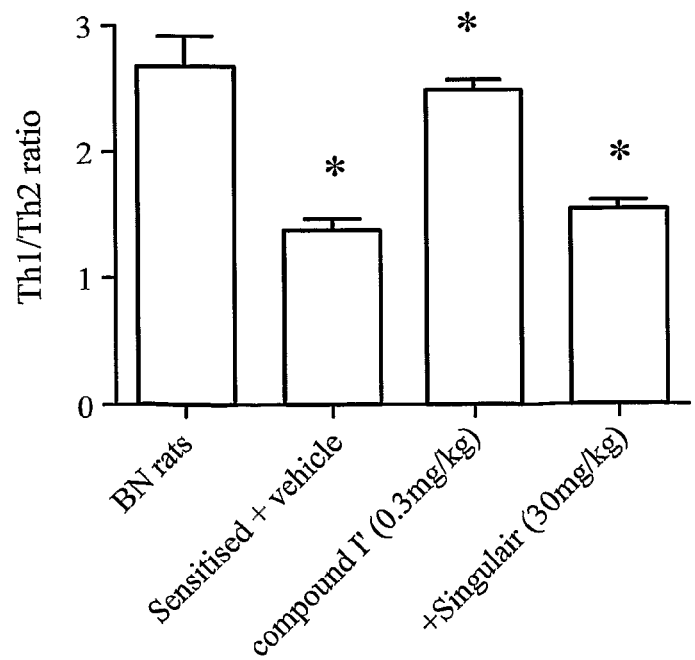

FIG. 9 shows the effect of compound (I') on T-helper cell polarisation in a representative experiment, as assessed by flow cytometric determination of IFN-γ (a Th1 marker cytokine) and IL-4 (a Th2 marker cytokine) production by CD4+ splenocytes in a rodent model of asthma. Bars represent mean Th1/Th2 ratios, shown on the Y-axis, for groups of 10 animals, whiskers represent SEM; *$p<0.05$ versus unchallenged rats; †$p<0.05$ versus sensitised and challenged rats, in both cases using Student's unpaired t-test assuming equal variance, with two tails). All rats (except the 'FIN rats' group, which was not exposed to ovalbumin) received the same sensitisation and challenge regimen, but were either treated with vehicle only ('Sensitised+vehicle'), or with compound (I') at 0.3 mg/kg bodyweight or with monteleukast ('Singulair™') at 30 mg/kg bodyweight, all administered daily by oral gavage.

Figure 10:
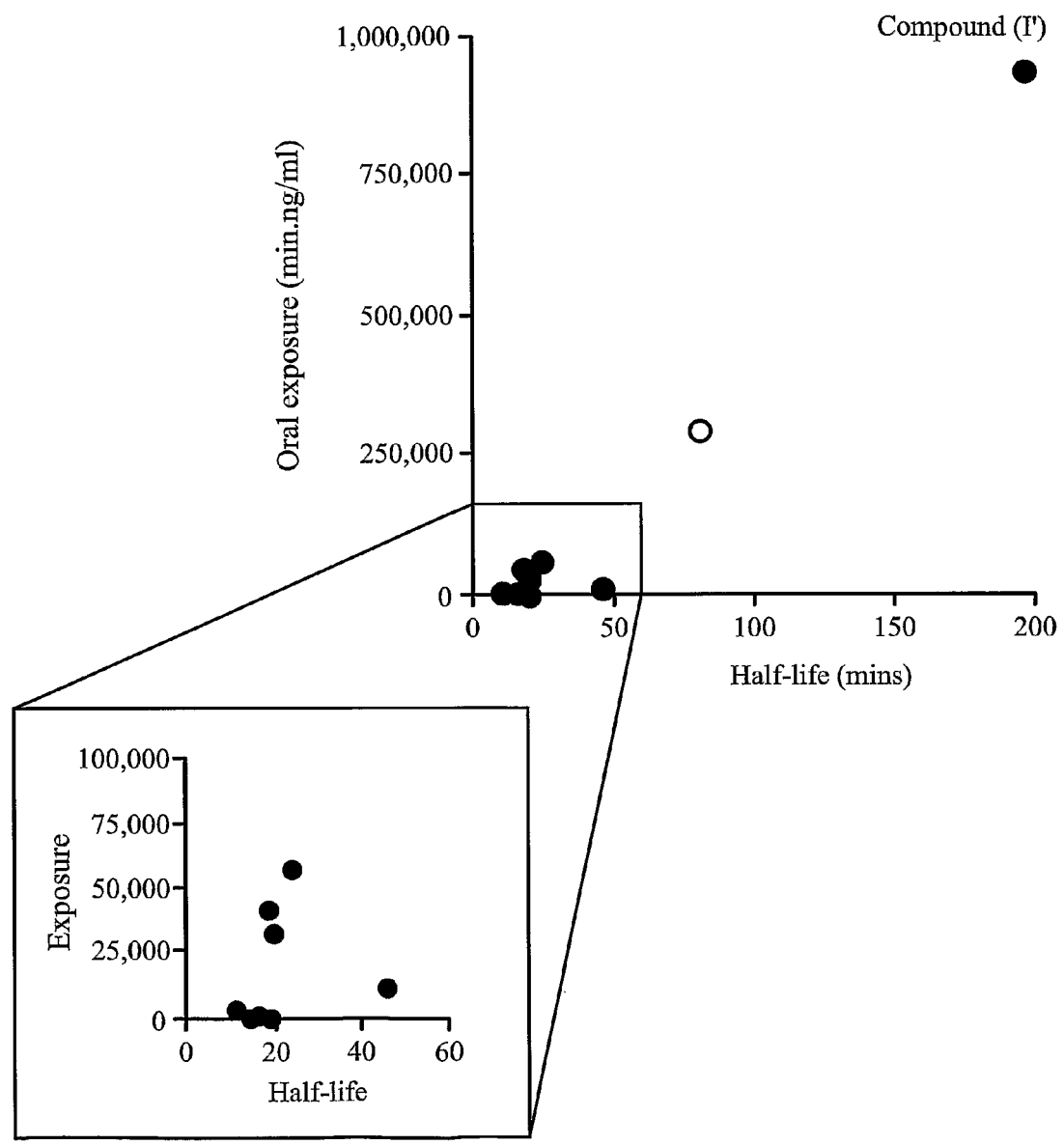

FIG. 10 is a plot of plasma half-life (in minutes) versus oral exposure for a range of different BSCI compounds in rat. In each case, the half-life was estimated using a standard one-compartment model of plasma concentrations at 0, 0.25, 0.5, 1, 2, 4, 6 and 8 hrs after a single iv bolus dose of the compound at 1 mg/kg dissolved in 1% CMC, 0.9% DMSO in saline. The oral exposure (AUCO-t in units of min·ng/ml) was calculated following a single oral dose of the compound at 3 mg/kg dissolved in 1% CMC, 0.9% DMSO in saline. The R-enantiomer of compound (I) which is the inversion of compound (I') and is identified as "(R)-(I)" is marked with an open circle.

EXAMPLES

In each of the following examples 1 through 6, (S)-3-(2',2'-dimethylpropanoylamino)-tetrahydropyridin-2-one (compound I') has been compared with a range of other lactam BSCIs which were selected to be representative of the various subclasses. For example, 3-(adamantane-1-carbonylamino)-caprolactam (II) was selected as typical of the subclass of polycycloacyl lactam BSCIs (such as those disclosed previously in WO2006/016152).

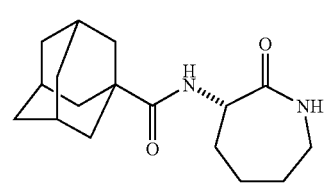

(II)

Similarly, 3-(1'-methylcyclohexylcarbonylamino)-caprolactam (III) was selected as typical of the subclass of monocycloacyl lactam BSCIs (such as those disclosed previously in WO2006/134384).

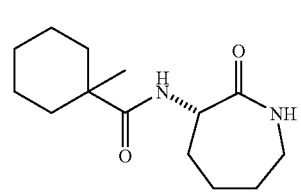

(III)

The compound 3-(1',1'-dimethylethylsulfonylamino)-caprolactam (IV) was selected as typical of the subclass of BSCIs with simple (noncyclic) alkyl side chains (such as those disclosed previously in WO2005/053702), as well as those with a sulfonylamino linker (as opposed to the carbon amide linker in the remaining compounds selected).

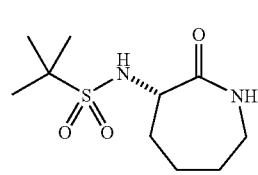

(IV)

The final compound selected, 3-(3'-hydroxyadamantyl-1-carbonylamino)-caprolactam (V) was typical of BSCIs with a substituted acyl side chain (whether simple linear, branched, mono- or polycyclo in structure).

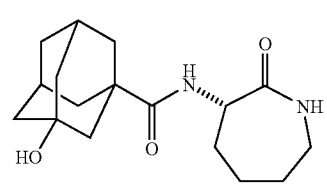

(V)

It is important to note that all of these BSCI compounds (II) through (V) have been specifically disclosed previously, and all have potent BSCI activity in vitro (ED50<1 nM for the inhibition of MCP-1 induced THP-1 cell migration). All have excellent stability in serum, in vitro, and from a theoretical perspective are all excellent candidates for development as human pharmaceuticals with anti-inflammatory properties in vivo.

All of the above compounds (I', II, III, IV and V) were tested in the (S) configuration at the lactam stereocentre.

Example 1

Pharmacokinetics Following a Single Dose

Compounds were administered as a single dose (either 1 mg/kg bodyweight in 5% DMSO via the intravenous route or 3 mg/kg in 1% carboxymethylcellulose via the oral route) to three adult rats (using different rats for each compound and each route of administration).

Blood was then sampled at various time points (including just prior to dose administration) out to 24 hrs post dose, and the level of the various compounds was assessed using a validated LC-MS/MS assay. Briefly, 3-5 µl of the deproteinised sample was applied to a Waters Atlantis (C18 20×2.1 mm, 3 µm bead size) reverse phase chromatography column equilibrated in 0.1% formic acid in 95:5 water:actetonitrile. Over 3.5 minutes bound material was gradient eluted reaching 0.1% formic acid in 5:95 water:acetonitrile, followed by a step gradient back to 0.1% formic acid in 95:5 water:acetonitrile. The column eluent was then directed to an Applied Biosystems API 4000/3200 QTrap MS/MS mass spectrometer, with a TurboIonspray™ ion source operating in positive ion mode. The interface temperature was set at 650° C., with a 40 ms dwell time for each MRM transition, monitoring the following ions:

| Analyte | Q1 Mass (amu) | Q3 Mass (amu) |
|---|---|---|
| (II) | 291.14 | 135.1 |
| (III) | 253.16 | 97.0 |
| (V) | 307.15 | 151.1 |
| (I') | 199.15 | 57.2 |
| (IV) | 249.15 | 129.3 |
| Internal standard | 213.19 | 57.1 |

The internal standard in each determination was the related compound (S)-3-(2',2'-dimethylpropanoylamino)-caprolactam, which was spiked into the sample prior to deproteinization. The lower limit of quantitation (LLOQ) for this assay was 2.4 ng/ml for each compound except (I'), where it was 38.1 ng/ml.

Following LC-MS/MS analysis of each collected sample, the pharmacokinetic disposition of the compound was modelled using Kinetica software, a well known software package for such applications.

Results

The individual concentration versus time graphs for each rat treated with each compound via the oral route are shown in FIG. 1. It is immediately obvious that of these five structurally diverse lactam BSCIs only (IV), (V) and (I') achieve any appreciable oral exposure, and that of these (I') is substantially better than the others.

The parameters of a simple one-compartment pharmacokinetic model are shown in Table 1. Firstly, this demonstrates the superior exposure achieved with (I')—nearly 20-fold higher than the next best compound, (V). The reason for this superior exposure (which is calculated as the area under the concentration versus time curve, in the units of min·ng/ml) is also evident: the clearance of (I'), which is defined as the theoretical volume of blood which is completely cleared of drug each minute in the units ml/min/kg, is more than 10-times lower than for the other lactam BSCIs.

TABLE 1

Pharmacokinetic parameters for structurally diverse lactam BSCIs.

| | F (%) | t½ (mins) | Clearance (ml/min/kg) | Vss (L/kg) | Exposure (min · ng/ml) |
|---|---|---|---|---|---|
| (I') | 69 | 196 | 2.6 | 0.7 | 939,000 |
| (II) | <1 | 16 | 84 | 0.8 | 477 |
| (III) | 5 | 11 | 55 | 0.6 | 2,900 |
| (IV) | 45 | 19 | 32 | 0.6 | 41,400 |
| (V) | 59 | 24 * | 31 | 1.4 | 57,100 |

Oral bioavailability (F, %), dominant plasma half-life (t½, mins), clearance (ml/min/kg), volume of distribution (Vss, L/kg) and exposure (AUC 0–>infinity, min · ng/ml) from a simple one-compartment pharmacokinetic model for each compound, averaged across three rats.
* 24 mins is the dominant half-life for (V) accounting for the clearance of more than 95% of the injected dose; the minor t½β was 110 mins. In all cases the Cmax was achieved within 30 mins, consistent with optimal absorption.

The clearance of (II) and (III) approximates to the liver blood flow of the rat, strongly suggesting that both these compounds are metabolised almost completely on first pass through the liver. Similarly the clearances of both (IV) and (V) exceed renal blood flow in the rat by some 3-4 fold, again suggesting substantial metabolic clearance presumably also liver mediated. In marked contrast, the clearance of (I') at 2.6 ml/min/kg is less than half of renal blood flow (typically quoted as 7-9 ml/min/kg), which suggests minimal metabolic clearance. Since (I') is extremely water soluble, with a volume of distribution consistent with free equilibration in total body water (0.7 L/kg), it is likely that the clearance below renal blood flow represents reabsorption with water in the renal distal tubule (rather than, for example, reduced exposure to the kidney due to sequestration into lipophilic compartments).

Consistent with the much lower clearance for (I') compared with the other compounds, (I') has a substantially longer plasma half-life (more than 3 hours, compared with less than half-an-hour for the other four compounds).

Not all of the BSCIs are observed to have oral bioavailability, even though all five of the chosen compounds were known to have oral bioactivity on acute inflammation end-points. This likely reflects the rapid liver-mediated metabolism of (II) and (III), which are absorbed efficiently but converted on first pass through the liver to metabolites which retain some activity as BSCIs (see example 2).

Based on this pharmacokinetic analysis, it will be obvious to those skilled in the art that despite the similar chemical stability and in vitro stability in isolated serum for these five compounds, as well as their similar predicted properties on theoretical grounds, nevertheless (I') is markedly superior to all the others. In particular, the clearance of the compound is much lower, probably reflecting a reduced propensity to liver-mediated metabolism, resulting in a 10-fold longer plasma half-life and almost 20-fold better oral exposure than the next best compound examined.

In a separate experiment, (I') was compared with the second best compound (V) for pharmacokinetic parameters in a different (non-rodent) species, the dog. Single doses (1 mg/kg in 5% DMSO intravenously or 3 mg/kg in 1% CMC per os) were administered to a single dog for each compound in a simple crossover design with 1 week washout between the two routes of administration.

The results are shown in Table 2.

TABLE 2

Comparison of the pharmacokinetic parameters for the best two lactam BSCIs in rat and dog.

Intravenous PK (1 mg/kg)

| Compound | Species | Half-life (mins) | Clearance (ml/min/kg) | Vss (L/kg) |
|---|---|---|---|---|
| (V) | Rat | 24 | 33 | 0.8 |
|  | Dog | 66 | 7.4 | 0.6 |
| (I') | Rat | 196 | 2.6 | 0.7 |
|  | Dog | 236 | 1.9 | 0.6 |

Oral PK (3 mg/kg)

| Compound | Species | Tmax (mins) | Half-life (mins) | Bioavailability (%) | AUC (min · ng/ml) |
|---|---|---|---|---|---|
| (V) | Rat* | 15 | 24 | 59 | 57100 |
|  | Dog | 60 | 67 | 59 | 240000 |
| (I') | Rat | 15-120 | 226 | 81 | 939000 |
|  | Dog | 60 | 217 | 75 | 1210638 |

The pharmacokinetics in dog are broadly similar to rat. In both species, compound (I') having considerably lower clearance, longer plasma half-life and hence greater exposure (AUC in min · ng/ml). In each case the predominant half-life (the faster $t^{1/2}\alpha$) is responsible for clearing more than 95% of the injected dose.

These observations indicate that the superior pharmacokinetic properties of (I') are not species specific and are consequently very likely also to be observed in humans.

Example 2

Identification of the Primary Metabolites

Urine was collected from rats exposed to a single oral dose (3 mg/kg in 1% CMC) of each compound over a 24 hour period in metabolic cages. The pooled urine sample was then subjected to full scan mass spectral analysis, using the same LC-MS conditions as described in example 1 above. Further MS-MS analysis of the product ions was then performed, and likely fragmentations/re-arrangements assigned from the publicly available Metabolite ID database.

For the major metabolites, the assigned structures were confirmed by synthesis of authentic samples, using methods well known in the art, which were subject to LC-MS-MS analysis under the same conditions as the urine samples.

Note that metabolite ID studies provide only qualitative estimates of the relative amounts of the different metabolites present, and separately validated assays with appropriate internal standards would be required to quantitate each metabolite species.

Results

The detected metabolites, in rank order of concentration detected are shown in FIG. 2 for the five compounds analysed. It is important to note that the methodology used here is not necessarily exhaustive, and further (particularly minor) metabolites may also be present which were below the detection limits for the methods applied here. As a general rule, it can be assumed that metabolites representing 10% or more of the injected dose will be detected (though not necessarily structurally identified) by the methods used here.

For compounds (II) and (III) the major route of metabolism is cytochrome P450-mediated hydroxylation, consistent with the rapid clearance at a rate approaching liver blood flow (see example 1 above). The major site of hydroxylation in both compounds is on the cycloalkyl tail group, with a second (slower) hydroxylation occurring on the lactam head group.

Note that the lactam hydroxylation products appeared in the MS-MS at −2 amu (as opposed to +16 amu) because of the instability of the 7-hydroxy adducts in the electrospray source.

For compound (II) the dihydroxylated product was present in sufficient quantity to be detected in urine, whereas for compound (III) no dihydroxylation product was detected. In both cases, it is likely that additional minor products were also formed below the level of detection of the method applied (for example, the 3,5 dihydroxy and 3,5,7 trihydroxy adamantyl derivatives of (II), as well as the glucuronidated adducts of both hydroxy-(II) and hydroxy-(III), particularly since the glucuronidated adduct of (V) was detected).

For compound (V) the glucuronidated compound was the major metabolite, although in rat only a minor fraction of the glucuronate is eliminated in urine, the bulk passing into faeces (in marked contrast to humans, where this glucuronidated adduct would be primarily excreted in urine). It is possible that other phase II metabolites (such as the 3'-O-sulphate) were also formed, but only at levels (at least in urine) too low to be detected by the methods used here. As for compounds (II) and (III), a small amount of product hydroxylated on the lactam head group was also detected (again primarily as a −2 amu product ion).

For compound (IV) the major metabolite could not be identified, although the loss of parent compound (see Table 3) was clearly consistent with the formation of an unidentified metabolite (less than 10% of the injected dose of (IV) was recovered unchanged. Given that compound (IV) was the only agent containing a sulfonamide linkage it is plausible, but currently unproven, that metabolic cleavage (or other modification) of the linker was occurring. Once again, a small amount of hydroxylation at the lactam head group was also observed.

In marked contrast to all the other compounds, no significant metabolites of (I') were detected in urine, consistent with the appearance of the majority of the injected dose in the urine in unchanged form (see Table 3) and the clearance rates at or below renal blood flow (see example 1 above). This lack of formation of metabolites is a major, and unexpected, advantage of (I') over the other compounds tested here for development as a human pharmaceutical and is, at least in part, responsible for the superior pharmacokinetic properties described in example 1 above.

To provide a quantitative estimate of the degree of metabolism suffered by each of the compounds tested, the amount of unchanged parent compound in urine was measured using the same validated LC-MS assay described in example 1, using (S)-3-(2',2'-dimethylpropanoylamino)-caprolactam as an internal standard. The results are shown in Table 3. In addition, the level of compounds in various target tissues was also determined.

TABLE 3

Distribution of compounds into various tissues 24 hrs after a single dose in rat.

| Compound | Heart | Lung | Kidney | Liver | Muscle | Brain | Urine (ng/ml) |
|---|---|---|---|---|---|---|---|
| (II) | nd | nd | nd | nd | nd | nd | nd |
| (III) | nd | nd | nd | nd | nd | nd | nd |
| (V) | nd | nd | nd | nd | nd | nd | 16300 |

TABLE 3-continued

Distribution of compounds into various tissues
24 hrs after a single dose in rat.

| Compound | Heart | Lung | Kidney | Liver | Muscle | Brain | Urine (ng/ml) |
|---|---|---|---|---|---|---|---|
| (I') | 5.3 | 21.9 | 5.1 | 3.6 | 3.1 | 1.6 | 24567 |
| (IV) | nd | nd | nd | nd | nd | nd | 1010 | nd = not detected; LLOQ = 2.4 ng/g
Only compounds (I'), (V) and (IV) were detectable in urine at 24 hrs after a single oral dose (3 mg/kg in 1% CMC). Of these, compound (I') underwent significantly less metabolism (more than 60% of the injected dose was recovered in urine). Furthermore, only compound (I') could be detected in any of the other tissues examined 24 hrs after a single dose. This likely reflects both the superior distribution and increased exposure associated with (I') compared to the other compounds tested here.

The much lower rate of metabolism of (F) compared to the other compounds demonstrates that, unexpectedly, (I') is markedly superior to the wide range of lactam BSCIs previously disclosed for development as a human pharmaceutical. This reduced metabolism (and hence improved ADME properties) likely accounts for the dramatically superior pharmacokinetic properties shown in example 1 above. Furthermore, since BSCIs are intended for development as anti-inflammatory agents targeting inappropriate leukocyte recruitment into a wide range of tissues, the unexpected finding that (I') is found in all tissues of the body tested 24 hrs after a single dose, whereas all the other lactam BSCIs tested were not, unequivocally demonstrates the particular utility of this novel compound.

Example 3

Safety Pharmacology

The five compounds were subjected to a standard AMES test to assess likely genotoxicity. Three His-auxotroph strains of *S. Typhinurium* (TA102, TA98 and TA100) were treated with each of the compounds at 5 concentrations (up to 5 mg/ml) in the presence and absence of S9 rat liver microsomal metabolising system. The number of revertant colonies was then determined by plating on trace-His minimal media.

The results (Table 4) show that none of the five compounds significantly increase revertant colony formation (with or without metabolic activation) in any of the strains tested.

TABLE 4

Revertant colony formation in AMES test.

| Compound | TA100 | TA100 + S9 | TA102 | TA102 + S9 | TA98 | TA98 + S9 |
|---|---|---|---|---|---|---|
| (II) | 0.59 * | 0.73 | 0.50 * | 0.93 | 0.58 * | 0.60 * |
| (III) | 0.79 | 0.81 | 0.69 | 0.88 | 0.68 | 0.55 |
| (V) | 0.78 | 0.88 | 0.93 | 1.09 | 0.96 | 0.91 |
| (I') | 0.97 | 0.95 | 0.82 | 0.93 | 2.00 ** | 1.23 |
| (IV) | 0.89 | 0.90 | 0.85 | 0.88 | 0.82 | 0.90 |
| +ve control | 6.89 | 7.18 | 5.97 | 2.65 | 9.68 | 19.05 |

At 5 mg/ml:
* = sparse bacterial background lawn
** = low control value in this experiment
= significant increase in revertant colonies
None of the compounds tested caused a significant increase in revertant colony formation at any of the concentrations tested (data for the top dose only is shown). Note that compound (II) caused inhibition of bacterial lawn growth at 5 mg/ml.

In a separate experiment, all five compounds were tested for interaction with the hERG ion channel. Compounds which interact with hERG are at risk of causing QT prolongation and potentially fatal cardiac arrhythmia. Compounds which inhibit hERG tail current by more than 50% at 10 μM are generally considered high risk for development as human pharmaceuticals.

HEK239 cells stably transfected to express hERG were perfused with bath solution containing the compounds at 10 μM (0.1% DMSO). hERG tail currents from three cells were then recorded by patch-clamp analysis following depolarisation to +20 mV for 5 s. The potency of the hERG interaction was then determined in a 4-point dose-response curve for any compounds showing significant modulation at 10 μM.

The results (FIG. 3) show that none of the five compounds significantly interacted with the hERG channel at 10 μM.

We conclude that, from a safety pharmacology perspective, all five of the compounds, including (I') are equally suitable for development as human pharmaceuticals. In particular, the considerably superior ADME and pharmacokinetic properties of (I'), illustrated in Examples 1 and 2 above, are not accompanied by correspondingly worse safety pharmacology profiles.

Example 4

General Pharmacology

The general pharmacology of the five compounds was assessed, both against the specific target receptor, and against a wide variety of other receptors, many related in structure to the target receptor. Specific binding to the target receptor was assessed by competition for the binding of [$^3$H]-BN83250 (BN83250 is (S)-3-(2',2'-dimethyldodecanoylamino)-caprolactam; Fox et al. J Med. Chem. 200; 48(3):867-74; an agent known to bind to the same target receptor as the lactam BSCIs disclosed here). Binding to non-target receptors was assessed by competition for the binding of various specific radioligands for other receptors which are well known in the art.

For specific binding the human myelomonocytic cell line was resuspended in binding buffer (20 mM HEPES, 150 mM NaCl, pH 7.4; 10$^6$ cells per reaction) at 4° C. in the presence of 10 nM [$^3$H]-BN83250 (from 1 μM stock in 100% ethanol; 30 Ci/mmol) and various competitors (1% DMSO maximum vehicle concentration). Reactions were incubated for 2 hours on ice, then filtered through GF/C filters pre-soaked in 0.5% polyethyeneimine. Unbound material was washed away with 5×5 ml ice cold washing buffer (20 mM HEPES, 150 mM NaCl, pH 7.4) under a slow vacuum. These conditions have previously been shown to achieve equilibrium binding, with at least 80% of the binding specific (competable with 10 μM cold BN83250).

Competition for the specific [³H]-BN83250 with compounds (I'), (II) and (V) was then determined at various concentrations from 1 pM to 10 pM. Compounds (III) and (IV) were not examined in these experiments. A typical competition binding curve for (I') is shown in FIG. 4.

Non-linear modelling was then applied to the competition binding curves for the various compounds, in order to compare their properties as agents binding to the target receptor (defined as the site of specific interaction of BN83250). The parameters of the resulting models are given in Table 5.

TABLE 5

Non-linear modeling of competitive binding curves.

| Compound | Functional ED50 versus MCP-1 (pM) | Ka at target receptor (pM) | Hill slope |
|---|---|---|---|
| (II) | 80 | 8,200 | −0.5 |
| (III) | 80 | Not tested | Not tested |
| (V) | 120 | 10,000 | −0.5 |
| (I') | 50 | 50 | −1.0 |
| (IV) | 800 | Not tested | Not tested |

It is important to note that compound (I'), in marked contrast to lactam BSCIs (II) and (V), showed ideal and predictable binding to the target receptor. In particular, the apparent affinity for binding to the receptor was of a similar magnitude to the functional ED50 value in migration inhibition assays. Similarly, the Hill Slope was approximately −1.0 (the theoretically expected value for a simple, non-cooperative competitive binding model), whereas the other lactam BSCIs showed considerably shallower Hill Slopes. The cause of the departure from ideal binding to the target receptor for compounds (II) and (V) is not known, but this difference further underlines the unexpected superiority of compound (I').

Binding to non-target receptors was assessed using similar protocols, exploiting specific radioligands for each receptor which are well known in the art. Each compound was tested for competition against the specific binding of each ligand only at a single concentration (10 μM). Where the inhibition of binding was between 20% and 80%, the Ka for the interaction was estimated. Where the inhibition was <20%, the compound was assumed to have no competitive interaction with the receptor. Where the inhibition was >80% the Ka was reported as <1 μM. Details of the receptors screened, and the radioligands and cell types used in the assays, are available at www.cerep.fr The results (FIG. 5) demonstrate that all of the lactam BSCI compounds tested are devoid of major cross-reactivities based on this panel of 75 receptors (no interactions with an estimated Ka<1 μM were noted). Only one weak (but statistically significant) cross-reaction was noted (compound (II) with the NK2 receptor). On this basis, compound (I') was marginally more specific for the target receptor than (II), but all the lactam BSCI compounds tested were suitable for development as human pharmaceuticals based on their lack of off-target binding identified in this high throughput screening assay format.

Example 5

Broad-Spectrum Chemokine Inhibition Activity In Vitro

The biological activity of the compounds of the current invention may be demonstrated using any of a broad range of functional assays of leukocyte migration in vitro, including but not limited to Boyden chamber and related transwell migration assays, under-agarose migration assays and direct visualisation chambers such as the Dunn Chamber.

For example, to demonstrate the inhibition of leukocyte migration in response to chemokines (but not other chemoattractants) the 96-well format ChemoTx™ micro transwell assay system from Neuroprobe (Gaithersburg, Md., USA) has been used. In principle, this assay consists of two chambers separated by a porous membrane. The chemoattractant is placed in the lower compartment and the cells are placed in the upper compartment. After incubation for a period at 37° C. the cells move towards the chemoattractant, and the number of cells in the lower compartment is proportional to the chemoattractant activity (relative to a series of controls).

This assay can be used with a range of different leukocyte populations. For example, freshly prepared human peripheral blood leukocytes may be used. Alternatively, leukocyte subsets may be prepared, including polymorphonuclear cells or lymphocytes or monocytes using methods well known to those skilled in the art such as density gradient centrifugation or magnetic bead separations. Alternatively, immortal cell lines which have been extensively validated as models of human peripheral blood leukocytes may be used, including, but not limited to THP-1 cells as a model of monocytes or Jurkat cells as model of naïve T cells.

Although a range of conditions for the assay are acceptable to demonstrate the inhibition of chemokine-induced leukocyte migration (see for example the advice provided by Frow et al. Med Res Rev. 2004; 24(3):276-98 on the conditions required to interpret in vitro migration assays), a specific example is hereby provided.

Materials

The transwell migration systems are manufactured by Neuroprobe, Gaithersburg, Md., USA. The plates used are ChemoTx™ plates (Neuroprobe 101-8) and 30 μl clear plates (Neuroprobe MP30).

Geys' Balanced Salt Solution is purchased from Sigma (Sigma G-9779). Fatty acid-free BSA is purchased from Sigma (Sigma A-8806). MTT, i.e. 3-(4,5-dimethylthiazol-2-yl)-2,5-diphenyltetrazolium bromide, is purchased from Sigma (Sigma M-5655). RPMI-1640 without phenol red is purchased from Sigma (Sigma R-8755).

The THP-1 cell line (European Cell Culture Collection) were used as the leukocyte cell population.

Test Protocol

The following procedure is used for testing the compound of the present invention for the ability to specifically block leukocyte migration induced by chemokines:

First, the cell suspension to be placed in the upper compartment is prepared. The THP-1 cells are pelleted by centrifugation (770×g; 4 mins) and washed with Geys Balanced Salt Solution with 1 mg/ml BSA (GBSS+BSA). This wash is then repeated, and the cells repelleted before being resuspended in a small volume of GBSS+BSA for counting, for example using a standard haemocytometer.

The volume of GBSS+BSA is then adjusted depending on the number of cells present so that the cells are at final density of 4.45×10⁶ cells per ml of GBSS+BSA. This ensures that there are 100,000 THP-1 cells in each 25 μl of the solution that will be placed in the upper chamber of the plate.

To test a single compound for its ability to inhibit chemokine induced migration, it is necessary to prepare two lots of cells. The suspension of THP-1 cells at 4.45×10⁶ cells/ml is divided into two pots. To one pot the inhibitor under test is added at an appropriate final concentration, in an appropriate vehicle (for example at 1 μM in not more than 1% DMSO). To the second pot an equal volume of GBSS+BSA plus vehicle as appropriate (e.g. not more than 1% DMSO) is added to act as a control.

Next, the chemoattractant solution to be placed in the lower compartment is prepared. For example, MCP-1 is diluted in GBSS+BSA to give a final concentration of 25 ng/ml. This is divided into two pots, as for the cell suspension. To one pot, the test compound is added to the same final concentration as was added to the cell suspension, while to the other pot an equal volume of GBSS+BSA plus vehicle as appropriate (e.g. not more than 1% DMSO) is added. Alternatively, other chemokines may be used (SDF-1α at 7.5 ng/ml; RANTES at 50 ng/ml; IL-8 at 10 ng/ml using neutrophils as the target cell population). In each case it is important to determine (in a separate experiment) the concentration of each chemokine which causes maximal stimulation of migration of the chosen target leukocyte population. This maximal concentration must then be used in experiments to test the inhibitory activity of the compounds of the invention. Because chemokines typically induce leukocyte migration with a bell-shaped dose-response curve, the use of a sub- or supra-maximal chemokine concentration can lead to artefactual results (for example, a compound which is a chemokine inhibitor can yield a paradoxical stimulation of leukocyte migration if a supra-maximal concentration of chemoattractant is incorrectly selected for the experimentation. Further illustrations of this important factor in the design of in vitro leukocyte migration experiments has are provided by Frow and colleagues (*Med Res Rev.* 2004; 24(3):276-98). In addition, non-chemokine chemoattractants may also be used to demonstrate the chemokine-selectivity of the biological activity of the compounds of the invention (for example C5a at 25 ng/ml using neutrophils as the target cell population or TGF-β1 at 10 ng/ml using THP-1 cells as the target population).

Note that the volume of liquid that needs to be added with the addition of the test compound needs to be taken into account, when establishing the final concentration of MCP-1 in the solution for the lower compartment and the final concentration of cells in the upper compartment.

Once the chemoattractant solutions for the lower wells and cell solutions for the upper chambers have been prepared, the migration chamber should be assembled. Place 29 µl of the appropriate chemoattractant solution into the lower well of the chamber. Assays should be performed with at least triplicate determinations of each condition. Once all the lower chambers have been filled, apply the porous membrane to the chamber in accordance with the manufacturer's instructions. Finally, apply 25 µl of the appropriate cell solution to each upper chamber. A plastic lid is placed over the entire apparatus to prevent evaporation.

The assembled chamber is incubated at 37° C., 5% $CO_2$, for 2 hours. A suspension of cells in GBSS+BSA is also incubated under identical conditions in a tube: these cells will be used to construct a standard curve for determining the number of cells that have migrated to the lower chamber under each condition.

At the end of the incubation, the liquid cell suspension is gently removed from the upper chamber, and 20 µl of ice-cold 20 mM EDTA in PBS is added to the upper chamber, and the apparatus is incubated at 4° C. for 15 mins. This procedure causes any cells adhering to the underside of the membrane to fall into the lower chamber.

After this incubation the filter is carefully flushed with GBSS+BSA to wash off the EDTA, and then the filter is removed.

The number of cells migrated into the lower chamber under each condition can then be determined by a number of methods, including direct counting, labelling with fluorescent or radioactive markers or through the use of a vital dye. Typically, we utilise the vital dye MTT. 3 µl of stock MTT solution are added to each well, and then the plate is incubated at 37° C. for 1-2 hours during which time dehydrogenase enzymes within the cells convert the soluble MTT to an insoluble blue formazan product that can be quantified spectrophotometrically.

In parallel, an 8-point standard curve is set up. Starting with the number of cells added to each upper chamber (100,000) and going down in 2-fold serial dilutions in GBSS+BSA, the cells are added to a plate in 25 µl, with 3 µl of MTT stock solution added. The standard curve plate is incubated along side the migration plate.

At the end of this incubation, the liquid is carefully removed from the lower chambers, taking care not to disturb the precipitated formazan product. After allowing to air dry briefly, 20 µl of DMSO is added to each lower chamber to solubilise the blue dye, and absorbance at 595 nm is determined using a 96-well plate reader. The absorbance of each well is then interpolated to the standard curve to estimate the number of cells in each lower chamber.

The chemoattractant stimulated migration is determined by subtracting the average number of cells that reached the lower compartment in wells where no chemoattractant was added from the average number of cells that reached the lower compartment where the chemoattatractant was present.

The impact of the test substance is calculated by comparing the chemoattractant-induced migration which occurred in the presence or absence of various concentrations of the test substance. Typically, the inhibition of migration is expressed as a percentage of the total chemoattractant-induced migration which was blocked by the presence of the compound. For most compounds, a dose-response graph is constructed by determining the inhibition of chemoattractant-induced migration which occurs at a range of different compound concentrations (typically ranging from 1 nM to 1 µM or higher in the case of poorly active compounds). The inhibitory activity of each compound is then expressed as the concentration of compound required to reduce the chemoattractant-induced migration by 50% (the $ED_{50}$ concentration). Typically, MCP-1 induced migration of THP-1 cells has been used as the standardised test system for the comparison of the biological activity of a wide range of compounds (see for example Reckless & Grainger *Biochem J.* 1999 Jun. 15; 340 (Pt 3):803-11; Reckless et al. *Immunology.* 2001 June; 103 (2):244-54; Fox et al. *J Med. Chem.* 2002 Jan. 17; 45(2):360-70; Fox et al. J Med. Chem. 2005 Feb. 10; 48(3):867-74; the International applications supra). Compounds which inhibit leukocyte migration induced by more than one chemokine, but not by non-chemokine chemoattractants (such as TGF-β or C5a) are defined as Broad-spectrum Chemokine Inhibitors (BSCIs; see for example Grainger & Reckless *Biochem Pharmacol.* 2003 Apr. 1; 65(7):1027-34; Grainger et al. *Mini Rev Med. Chem.* 2005 September; 5(9):825-32).

Results

A typical dose response curve for compound (I') inhibiting MCP-1 induced migration of THP-1 cells is shown in FIG. 6, together with comparable dose response curves for other selected lactam BSCIs known to have particularly high (that is, <1 nM) potency. The potency of compound (I') versus various chemokines and non-chemokine chemoattractants, expressed as ED50 values is shown in Table 6, and is compared with other lactam BSCIs described previously.

It is clear from this data that compound (I') can be classified as a BSCI (since it powerfully and potently inhibits leukocyte migration induced by a range of chemokines, but has no effect on leukocyte migration induced by a non-chemokine chemoattractant, in this case the C5a anaphylatoxin). Furthermore, it is evident that compound (I') is at least as potent and powerful as a BSCI in vitro as the selected lactam BSCIs which have previously been disclosed (for example, compound (II) in WO2006/016152 or compound (IV) in WO2005/053702). All of the lactam BSCIs examined here are considerably more potent than any of the non-lactam BSCIs which have been disclosed to date (including imides, such as NR58,4, yohimbamides, lysergamides and peptide 3 and related structures such as NR58-3.14.3). Indeed, compound (I') is more potent as a BSCI in vitro (at least against MCP-1 induced migration) than any other compound disclosed or described previously. Although this potency as a BSCI is quantitatively superior to BSCIs in the prior art (albeit to a small degree), it is not this property that primarily marks out compound (I) as unexpectedly superior to the prior art BSCIs. Instead, this demonstrates that the unexpected, and substantially superior, ADME and pharmacokinetic properties of compound (I) compared to a wide range of previously disclosed BSCIs, has been achieved with no loss of power or potency as a BSCI in vitro.

TABLE 6

Effect of selected lactam BSCIs on leukocyte migration in vitro.

| Compound | MCP-1 | SDF-1α | RANTES | IL-8 neutrophils | C5a neutrophils |
|---|---|---|---|---|---|
| (II) | 80 | 100 | 100 | 600 | >1,000,000 |
| (III) | 80 | Not tested | Not tested | Not tested | Not tested |
| (V) | 120 | 200 | 250 | 500 | >1,000,000 |
| (I') | 50 | 50 | 80 | 600 | >1,000,000 |
| (IV) | 800 | Not tested | Not tested | Not tested | Not tested |

In each case the dose of compound (in pM) required to inhibit leukocyte migration in response to a maximal dose of the stated chemoattractant by 50% (the ED50) is shown. Unless stated otherwise, the data is reported for the THP-1 cell lines. For C5a induced migration none of the compounds tested inhibited neutrophil migration to any degree even at the highest concentration tested (1 μM).

Example 6

Anti-Inflammatory Activity In Vivo

We have used the sub-lethal LPS-induced endotoxemia assay to demonstrate the generalised anti-inflammatory properties in vivo of previously disclosed BSCIs (see, for example, Fox et al. *J Med. Chem.* 2002; 45(2):360-70; Fox et al. J Med. Chem. 2005; 48(3):867-74). In this assay, mice are given a non-specific pro-inflammatory challenge using bacterial endotoxin (LPS), and the extent of the systemic inflammatory response (measured by serum levels of the central pro-inflammatory cytokine TNF-α, which is essentially absent from the blood under normal conditions, but is rapidly elevated in response to a wide range of inflammatory stimuli). We have selected this model even though it is not, itself, a particularly close model of any human inflammatory disease condition, but because TNF-α is known to be important in very many diseases (including rheumatoid arthritis, autoimmune disorders, Crohn's Disease, atherosclerosis, asthma and many more). Consequently, agents which suppress TNF-α production are already used clinically (e.g. Enbrel™ and other anti-TNF-α antibody products) to treat a wide range of such diseases. Demonstration of TNF-α suppressive activity in this model is therefore highly predictive of a clinically useful anti-inflammatory effect in a wide range of diseases.

Mice (in groups of 6) were pretreated with various doses of each compound, either by the subcutaneous route 30 mins prior to LPS challenge, or by the oral route (via gavage) 60 mins prior to LPS. The mice were then challenged with an intraperitoneal injection of 750 μg of bacterial LPS and sacrificed 3 hours later. Serum was prepared from a terminal bleed by cardiac puncture, and the concentration of TNF-α is determined by ELISA (R&D Systems). In each experiment, a group of 6 mice receive no LPS to act as a negative control, and a second group receive only LPS (with no candidate inhibitor). The level of TNF-α in serum from these animals, which received LPS without drug pre-treatment, is arbitrarily set to 100% (and is typically of the order of 6,000 pg/ml, compared with levels of <10 pg/ml among the negative control group). We have previously shown that the synthetic corticosteroid dexamethasone (itself a well known anti-inflammatory medicament active in a wide range of inflammatory diseases) inhibits LPS-induced TNF-α production by at least 90% in this model, while thalidomide (another published inhibitor of TNF-α production, acting at the level of cellular TNF-α production rather than as a leukocyte recruitment inhibitor like the BSCIs described here) inhibits LPS-induced TNF-α production by about 60%.

The effect of compound (I') at various doses, as well as other selected lactam BSCIs, is shown in FIG. 7. As expected, the compound powerfully inhibits LPS-induced TNF-α production whether the compound is delivered via the subcutaneous route (circles) or oral route (triangles). At doses above 1 μg/mouse, LPS-induced TNF-α levels were generally suppressed by more than 90%, comparable to the effects of the corticosteroid dexamethasone.

The other lactam BSCIs tested also inhibited LPS-induced TNF-α in a dose-dependent manner (FIG. 7), although the potency in vivo of (I') was greater than any of the other compounds tested (and, indeed, greater than the potency of other lactam BSCIs previously disclosed elsewhere which have been tested in this assay). This quantitative (albeit small) increase in potency is not the primary reason that we hereby claim compound (I) as unexpectedly superior to the prior art BSCIs. Instead, this demonstrates that the unexpected, and substantially superior, ADME and pharmacokinetic properties of compound (I) compared to a wide range of previously disclosed BSCIs, has been achieved with no loss of power or potency as an anti-inflammatory agent in vivo. In addition, these findings clearly demonstrate the utility of (I) as an anti-inflammatory agent in vivo, in a model of inflammation which indicates utility in a wide variety of inflammatory diseases where increased TNF-α production is a component of the pathogenic mechanism.

It is important to note that the hyperacute inflammation observed in this model is particularly insensitive to the ADME and pharmacokinetic properties of the anti-inflammatory agents tested. Since the LPS stimulation is administered only 30 minutes after the drug, even agents with very short plasma residence times (such as compounds (II) and (III)) remain present in plasma at sufficient concentrations to elicit a powerful anti-inflammatory effect. While such a test, therefore, does not emphasise the superiority of the claimed compounds over the prior art, it nevertheless demonstrates the utility of the compound.

The utility of the claimed compound is further demonstrated by studies in an animal model of the human disease asthma (the hyperacute inflammatory response observed in response to LPS exposure may not be typical of any particular human disease, although it is clearly a useful model system of acute inflammation in general). In these studies, rodents (typically rats) are exposed to ovalbumin in accordance with the following experimental design.

Adult Brown Norway rats (200-300 g body weight; n=10 per group) were sensitised by a single intraperitoneal injection of 0.1 mg Ovalbumin on day 0. Each rat then received an intratracheal challenge with a solution of 1% ovalbumin (w/v) on day 8, and with 2% ovalbumin (w/v) on days 15, 18 and 21. The animals were then sacrificed 3 hours after the final challenge on day 21. Note that ovalbumin (Sigma; purest available grade) was made endotoxin-free by passage over EndoTrap™ Red columns (purchased from Cambrex; used in accordance with the manufacturer's instructions), and the endotoxin level was confirmed as <5 EU/mg protein using the LAL assay (QCL-1000™; Cambrex; performed in accordance with the manufacturer's instructions; 1 mg of standard endotoxin contains 900,000 EU/mg). This ensures that the lung inflammation response results from the allergic response to the ovalbumin protein, rather than from unintended LPS stimulation which occurs even with the highest purity grade commercial ovalbumin preparations, and therefore ensures the model more closely represents the underlying molecular pathology of human asthma.

One group of mice (acting as a baseline control) received no ovalbumin challenges, but were otherwise treated identically. A second group (positive control) received the challenges but no drug treatment. A third group were treated identically, but received daily dosage with compound (I') at a dose of 0.3 mg/kg via oral gavage from day 8 until day 21, with dosage being given 1 hr prior to any subsequent challenge with ovalbumin made on the same day. Compound (I') was administered as a sterile solution in endotoxin-free phosphate buffered saline. A fourth group received monteleukast (the active component of the commercially available asthma medication Singulair™) at 30 mg/kg via the oral route, in an identical treatment schedule to compound (I').

On sacrifice, total lung leukocyte recruitment was assessed by performing a broncheoalveolar lavage (BAL) using 4 lots of 3 ml sterile phosphate-buffered saline introduced through a tracheal cannula. For each animal, the BAL washes were combined, and the total cell population counted (using a haemocytometer). Additionally, the types of leukocyte present were estimated using a flow cytometer in accordance with procedures well known in the art.

The spleen was also removed from each mouse and placed in RPMI+10% FCS+antibiotics. The spleen was then pressed through fine-mesh (100 μm) nylon screens in a sterile sieve cup placed in a sterile petri dish to produce single-cell suspensions. The resulting cell suspension was then centrifuged (328 g; 5 mins) and washed in RPMI+10% FCS+antibiotics, before being resuspended in fresh media and counted using a haemocytometer.

$4 \times 10^6$ total splenocytes (excluding RBCs) in total were cultured (37° C.; 5% $CO_2$) in RPMI+10% FCS+antibiotics overnight in presence of 2 U/ml (10 ng/ml) murine IL-2 in 4 wells of a 96 well plate (100 μl volume per well/$1 \times 10^6$ cells/well) from each mouse. Approximately 24 hrs later, the 4 wells were split into two groups of 2 wells: one group were left untreated, while the second group were stimulated with 500 ng/ml Ionomycin and 50 ng/ml PMA for 4 hours at 37° C. During the last two hours of this incubation 10 μg/ml Brefeldin A (stock 1ng/ml in EtOH) was added to one well from each set. Brefeldin A blocks protein transport to golgi and therefore allows accumulation of proteins in ER.

The wells without Brefeldin A were incubated for a further 48 hours at 37° C. At the end of the incubation, the cell suspensions were centrifuged (328 g; 5 mins) and the supernatant was subjected to ELISA assays (R&D Systems; performed in accordance with the manufacturer's instructions) for murine IL-4 (a marker of Th2 cells) and murine interferon-γ (IFN-γ; a marker of Th1 cells).

The wells with Brefeldin A were stained for intracellular IL-4 and IFN-g immediately at the end of the four hour incubation as follows: cells were stained with anti-CD4-FITC antibody (eBioscience Rat IgG2b, Cat. Code. 11-0041) for 30 mins on ice, then washed in Dulbecco's PBS and fixed with 2% paraformaldehyde (final concentration) in Dulbecco's PBS for 20 mins. After fixation cells were made permeable with Dulbecco's PBS/1% BSA/0.5% saponin (Sigma S7900) for 10 mins at room temperature. The cells from each well were then split into three separate FACS tubes and incubated with:

IFN-g-PE (eBioscience Rat IgG1, Cat. Code. 12-7311-82, 100 μg) OR

Il-4-PE (eBioscience Rat IgG1, Cat. Code. 12-7041-82, 100 μg) OR

Isotype controls (a mixture of Rat IgG2b-FITC, eBioscience Cat. Code 11-4031 and Rat IgG1-PE, eBioscience Cat. Code 12-4301)

for 30 mins at room temperature. Cells were then washed (twice with PBS/BSA/saponin and then with PBS/BSA without saponin to allow membrane closure) and resuspended in Dulbecco's PBS ready for flow cytometry analysis.

Cells with specific staining for CD4 on the FITC channel (identifying them as T-helper cells) were analysed for the presence of specific staining for either IL-4 or IFN-g on the PE channel. The ratio of CD4+ cells staining positive for IFN-g to CD4+ cells staining positive for IL-4 was then reported as the Th1/Th2 ratio. Untreated Brown Norway rats have a Th1/Th2 ratio of approximately 2.7 in the spleen (that is, approximately 2.7 times more CD4+ cells in the spleen are synthesising INF-g as IL-4). Following sensitisation and repeated challenge with ovalbumin, the ratio had fallen to less than 1.5 demonstrating the marked Th2 polarisation which accompanies asthmatic changes in both rodents and humans (a lower Th1/Th2 ratio indicates relative Th2 polarisation, while an increasing Th1/Th2 ratio indicates a relative Th1 polarisation).

Daily dosing with both compound (I') and the positive-control comparator compound monteleukast significantly reduced the number of leukocytes in the BAL washes (70% reduction with compound (I'); p<0.01 Student's unpaired t-test; FIG. 8).

This unequivocally demonstrates that the compound of the invention has a useful anti-inflammatory effect in a model of human asthma, resulting from its ability to block leukocyte migration in response to chemokines. The magnitude of such an effect is at least comparable with that of commercially available medicaments intended for the treatment of human asthma (such as Singular™), while the excellent pharmacokinetic and biodistribution parameters of compound (I') are illustrated by the considerably increased potency compared to monteleukast (a dose of 30 mg/kg of monteleukast is required to generate a similar reduction in BAL leukocyte counts compared to a dose of only 0.3 mg/kg of compound (I')).

Daily dosing with compound (I'), but not with the positive-control comparator compound monteleukast, significantly reversed the Th2 polarisation (FIG. 9), which is considered a major driver of asthma pathogenesis both in the ovalbumin-induced lung inflammation model used here, and in human asthma. Treatment with compound (I') even at low doses such as 0.3 mg/kg via the oral route completely abolishes the Th2 polarisation caused by chronic exposure to allergens such as ovalbumin, such that the Th1/Th2 balance in animals treated with compound (I') is essentially indistinguishable from unchallenged Brown Norway rats.

It is interesting to note that other chronic inflammatory diseases, such as atherosclerosis, are associated with a Th1 (as opposed to a Th2) polarisation. In both types of diseases, the imbalance in the T-helper cell cytokine profile has been described as a major pathogenic cause of the chronic inflammatory component of the disease. In models of a disease associated with a Th1 polarisation (such as in atherosclerosis) we have previously observed a marked shift towards Th2 on treatment with BSCIs, such as compound (I') claimed here. Mice with a homozygous deletion of the gene encoding apoE (apoE−/− mice) develop several vascular lipid lesions, even on a normal chow diet, and have a Th1/Th2 ratio of approximately 8 (compared to 3.2 in the background C57B16 wild-type strain). However, following treatment with BSCIs for a 3 month period (from 12 weeks of age to 24 weeks of age, the period during which most of the lipid lesion development occurs) normalises the Th1/Th2 ratio (and even causes a Th2 polarisation at very high doses in this model). Taken together with the data in the ovalbumin-induced lung inflammation model of asthma, we have demonstrated that BSCIs are able to normalise or rebalance the T-helper cell cytokine production profile irrespective of whether the underlying pathogenic defect is a Th2 polarisation (as in asthma) or a Th1 polarisation (as in atherosclerosis). We believe that BSCIs are currently the only agents described which have this "rebalancing" effect on the T-helper cell population. These mechanistic insights further underpin (together with efficacy data in numerous animal models of different diseases with an inflammatory component) our claim that BSCIs, and in particular compound (I) claimed here (as a result of its unexpectedly superior pharmacokinetic and biodistribution properties) are useful as medicaments to treat an unusually broad range of conditions with an inflammatory component.

Example 7

Comparison of Compound (I') with Structurally Related Analogs

Having identified compound (I) as having surprisingly superior pharmaceutical properties, particularly with respect to its pharmacokinetics, compared to other acylaminolactam BSCIs, we next compared it directly with the most structurally similar analogs that have previously been disclosed.

The original panel of compounds compared in examples 1 through 6 had been assembled to be as structurally diverse as possible, within the boundaries of the previously disclosed acylaminolactam BSCIs. Compound (I) ensured that 6-membered lactam 'headgroups' were included in the panel, although there is no particular reason to assume they are generally superior (or indeed inferior) to the compounds with 7-membered lactam rings (see WO2006/134385 for an extensive comparison of acylaminolactam analogs of different ring sizes in terms of potency as BSCIs in vitro). Similarly, the panel included a single example of a sulfonamide linkage (IV) as distinct from the amide linker in the remaining molecules.

With respect to the 'tailgroups', the panel included two simple alkyl groups (both pivoyl) and three cyclic alkyl groups (a methylcyclohexyl group, and two admantanes, one of which was substituted). All five compounds shared the well-established 2'2-disubstitution with tetrahedral bond angles at the key carbon (at the 2 position relative to the carbonyl of the amide carbonyl, with 4 carbon atoms bonded to this key carbon in a tetrahedral arrangement). This 2'2'-disubstitution feature at the key carbon atom has already been disclosed (WO2006/016152) as conferring additional potency on BSCIs compared to linear alkyl 'tailgroups', or other structures lacking four carbon atoms bonded to this key carbon in an essentially tetrahedral arrangement.

As a result, the 'tailgroups' in the original panel were selected with the requirement of having this 2',2'-disubstitution feature, to ensure adequate in vitro potency, but also with the requirement of likely yielding acceptable physical properties in the resulting molecules. For example, it was expected that the adamantane, cyclohexyl and short chain 2'2-branched alkyl groups would result in compounds with crystalline (or semi-crystalline) solid forms, and with acceptable water solubility. In contrast, other possible tailgroups, such as 2',2'-dimethyldodecanoyl (which otherwise conforms to the desirable arrangement of carbon atoms at the key 2-position), were excluded from the panel on the basis of their waxy, amorphous physical forms as solids and their extreme insolubility in physiological buffers. Both of these factors reduce the desirability of a compound for pharmaceutical development even before the ADME and toxicological properties have been determined because they make the compound difficult to handle, for example during formulation or tableting, and this increases the likelihood of unfavourable ADME properties such as accumulation in fat stores during chronic dosing or lack of oral bioavailability.

Thus the five compounds examined in examples 1 through 6 had a roughly equal chance of being suitable for pharmaceutical development. Prior to determining their ADME properties it was not possible, to predict which would be superior.

Once the testing described in examples 1 through 6 was complete, however, it became clear than compound (I) was substantially and unexpectedly superior to the other compounds. Since compound (I) was the only compound in the panel with a 6-membered ring, it was possible that the superior properties were due to the size of the lactam ring. To determine whether this was true, we reviewed all the previously disclosed examples of acylaminolactam compounds with BSCI activity, and selected the two compounds with greatest structural similarity to (I). Of all the previously known compounds with BSCI activity, these were the two compounds with the most similar structure to compound (I).

The selected compounds were 3-(2',2'-dimethyldodecanoylamino)-tetrahydropyridin-2-one (example 3 from WO2006/134385; here designated VI) and 3-(adamanatane-1-carbonylamino)-tetrahydropyridin-2-one (example 1 from WO2006/134385; here designated VII):

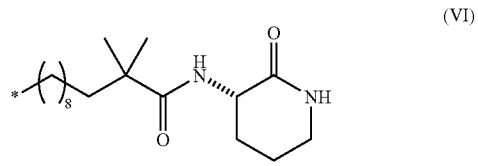

(VI)

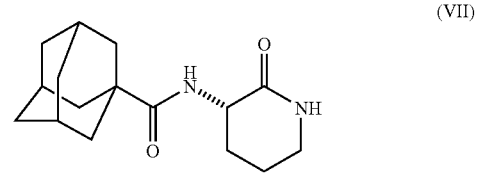

(VII)

These compounds share in common with (I) the 6-membered lactam ring, the amide linker and the presence of 2',2'- disubstitution, with 4 carbon atoms bonded to the key carbon at the 2-position relative to the amide carbonyl group, in an essentially tetrahedral arrangement.

Compounds (VI) and (VII) were subject to pharmacokinetic analysis in rat using exactly the same protocols previous applied for compounds (I) through (V) in example 1. Note that the (S) enantiomer of both (VI) and (VII) was used for these experiments, since this is expected to be the more active enantiomer in common with all other acylaminolactam BSCIs described to date.

Results

Unfortunately, (VI) was a waxy solid with a tendency to retain solvent. It was difficult to obtain a preparation of (VI) which was solvent-free, but this was eventually achieved after considerable drying over many weeks. However, this sample was completely insoluble in the 5% DMSO in saline, used as the vehicle for intravenous dosing of the previous compounds. As a result, it was necessary to use a wholly different vehicle in order to prepare a solution suitable for intravenous dosing.

Compound (VI) was dissolved in 50% PEG400/20% solutol/30% saline for intravenous dosing. All compounds, including (VI), were suspended (or dissolved) in 1% carboxymethylcellulose in saline for oral dosing. Although comparing oral bioavailability between experiments using different vehicles is not generally recommended (because the vehicle can have a considerable impact on gut absorption of compounds), it is nevertheless very unlikely that the selection of vehicle significantly affects the observed half-life following intravenous injection of (VI) compared with other compounds, such as (I).

The parameters of a simple one-compartment pharmacokinetic model are shown in Table 7. Data for compound (I') from Table 1 above is shown for comparison. It is evident that (VI) and (VII) are both markedly inferior to (I'), with clearance rates more than 10-fold higher, and oral exposure which is 25-50 fold less than was achieved with (I')

TABLE 7

Pharmacokinetic parameters for selected 6-ring acylaminolactam BSCIs.

|  | F (%) | t½ (mins) | Clearance (ml/min/kg) | Vss (L/kg) | Exposure (min · ng/ml) |
|---|---|---|---|---|---|
| (VI) | 16 | 46 | 40.3 | 1.95 | 11,000 |
| (VII) | 35 | 20 | 31.1 | 0.7 | 32,500 |
| (I') | 69 | 196 | 2.6 | 0.7 | 939,000 |

Oral bioavailability (F, %), dominant plasma half-life (t½, mins) following intravenous dosing, clearance (ml/min/kg), volume of distribution (Vss, L/kg) and oral exposure (AUC 0-t, min · ng/ml) from a simple one-compartment pharmacokinetic model for each compound, averaged across three rats. For (VII), Cmax was achieved within 15 mins, consistent with optimal absorption as for (I'). The hydrophobic (VI) was absorbed more slowly, however, with Tmax between 60 and 120 mins.

Indeed, it is evident from comparison of Table 7 with Table 1 that compounds (VI) and (VII) are not even as good as (IV) and (V) in tennis of exposure. Despite sharing the 6-lactam ring with (I), compounds (VI) and (VII) have markedly inferior ADME properties, and are no better than a wide range of other acylaminolactam BSCI compounds which have previously been disclosed.

Consistent with the much higher clearance for (VI) and (VII) compared with (I'), these compounds have substantially shorter plasma half-lives than (I') (less than 1 hour, compared with more than 3 hours).

Based on this pharmacokinetic analysis, it will be obvious to those skilled in the art that despite the similar chemical stability, as well as their similar predicted properties on theoretical grounds and their similarity in structure, nevertheless (I') is markedly superior to both (VI) and (VII), with 25-50 fold better oral exposure than the either of these 6-ring lactam analogs. We conclude that the unexpectedly excellent ADME properties of (I') cannot be attributed to the 6-ring lactam (since other 6-ring lactams, such as (VI) and (VII) do not share its outstanding ADME characteristics), nor to the amide linker (since other amide linker compounds, including (II), (III) and (V) do not share its outstanding ADME characteristics), nor to the pivoyl tail group (since compound (IV) shares this group and does not have the outstanding ADME characteristics of (I')). Instead, the surprising and markedly superior ADME characteristics of (I') depend on the particular combination of structural features, which could not be predicted.

Example 8

Attempt to Rationally Design an Acylaminolactam BSCI with ADME Properties Equivalent to (I')

In the process of identifying the superior ADME properties of compound (I'), we have analysed the pharmacokinetics of a variety of different acylaminolactams with sub-nanomolar potency as BSCIs in vitro. As a result, we would expect to have gained some insight into the factors which modulate ADME properties for molecules within this structural space. We therefore attempted to use this experience to select a second acylaminolactam BSCI compound from amongst the structural classes previously disclosed with ADME properties as similar as possible to those of (I').

The relatively rapid clearance of (IV) compared with (I') (see Table 1 above) suggested that the amide linker may be correlated with superior ADME properties. We therefore limited the selection to compounds with amide linkers.

Compound (II) was very well absorbed, but was rapidly converted to (V) in vivo, presumably through the action of liver cytochrome P450 isoenzyme(s). Compound (v) itself was not apparently further oxidised (probably as a result of the electron withdrawing substituent on the adamantine ring) but was nevertheless cleared relatively rapidly. The absence of detectable primary metabolites in the urine strongly suggests that the rapid clearance was mediated by the formation of a phase II conjugate, such as the glucuronide, which in rat is excreted in the faeces. Phase II conjugates are readily formed at hydroxyl groups, such as the 3-hydroxyadamantane in (V). As a result, we proposed that a derivative of (II) with a stable electron-withdrawing substituent (to prevent hydroxylation of the adamantine ring by cytochrome P450 or other liver hydroxylases or oxidases) which was unable to form phase II conjugates, such as a halo substituent, may have the optimal ADME properties we were seeking.

As a result, compound (VIII), below, was synthesised and tested. We selected the chloro-substituted analog (over the fluoro-substituted analog, for example) because this was a known compound (see example 8 in WO2006/016152) for which a synthetic route was readily available. Furthermore, introduction of aliphatic C—F bonds is challenging synthetically, and can increase the cost of goods for the active pharmaceutical ingredient by an order of magnitude or more.

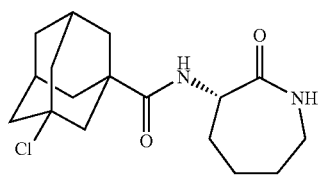

(VIII)

As previously (see Example 7), we elected to prepare and evaluate the (S)-enantiomer of this compound, since in general the (S)-enantiomers of acylaminolactam compounds are known to have greater BSCI activity in vitro.

An obvious concern related to this molecule was the stability of the C—Cl bond. We therefore examined the stability of (VIII) in vitro, both in physiological saline and in a rat liver microsome preparation. Encouragingly, less than 2% of (VIII) had undergone hydrolysis (determined by LC/MS, with dual ion detection of the hydrolysis product (V) and the parent compound (VIII)) even after 24 hours at 37° C. Similarly, incubation of (VIII) at 1 µM with a rat microsome preparation for 1 hour at 37° C. resulted in less than 10% degradation compared to a "no NADPH" blank run. As a result, we conclude that compound (VIII) has similar in vitro stability and intrinsic clearance to (I').

Thus, based on theoretical grounds using the experience gained from the discovery of (I'), as well as general skill in the art of predicting ADME properties, as well as using conventional in vitro screening assays, such as in vitro stability and intrinsic clearance in liver microscome preparations, compound (VIII) would be expected to have ADME properties comparable with (I').

We therefore subjected (VIII) to pharmacokinetic analysis in rat using exactly the same protocols previous applied for compounds (I') through (VII) in examples 1 and 7.

Results

The parameters of a simple one-compartment pharmacokinetic model are shown in Table 8. Data for compound (I') from Table 1 above is shown for comparison. It is evident that compound (VIII) is markedly inferior to (I'), with clearance rates more than 20-fold higher, and no detectable oral bioavailability whatsoever.

TABLE 8

Pharmacokinetic parameters for selected lactam BSCIs.

| | F (%) | t½ (mins) | Clearance (ml/min/kg) | Vss (L/kg) | Exposure (min · ng/ml) |
|---|---|---|---|---|---|
| (VIII) | <1% | 15 | 62.8 | 0.7 | <100 |
| (I') | 69 | 196 | 2.6 | 0.7 | 939,000 |

Oral bioavailability (F, %), dominant plasma half-life (t½, mins) following intravenous dosing, clearance (ml/min/kg), volume of distribution (Vss, L/kg) and oral exposure (AUC 0-t, min · ng/ml) from a simple one-compartment pharmacokinetic model for each compound, averaged across three rats. For (VIII), the level of analyte was below the limit of quantitation (~2 ng/ml) at all time-points following oral dosing.

In conclusion, compound (VIII), which we had selected on the basis of theoretical considerations and in vitro screening tests, to have optimal ADME properties was nevertheless among the least suitable acylaminolactam compounds, at least amongst those whose PK has been determined, for development as a pharmaceutical agent. The compound exhibited rapid clearance, resulting in a short plasma half-life and additionally showed no oral bioavailability whatsoever.

The extent of the superiority of compound (I') is illustrated in FIG. 10. Here, we have plotted two PK parameters (plasma half-life and oral exposure) for every BSCI compound for which the pharmacokinetics have been analysed in rat. Compound (I') lies far away from the cluster, representing the generally poor ADME properties of compounds in this structural space (and not untypical of very many entirely unrelated classes of drug candidates), indicating that compound (I') is unexpectedly, and unusually, superior.

Example 9

Comparison of the (S)- and (R)-Enantiomers of (I)

Compound (I') has been shown to have unexpected, and markedly superior, ADME properties (see example 1). This compound has an assymetrical carbon atom (at the ring junction with the amide linker) and consequently exists in two stereoisomers: the (S)-enantiomer designated (I') and the opposite (R)-enantiomer, designated (R)-(I).

As with all other acylaminolactam BSCIs described to date, the (S)-enantiomer of (I) is more potent as a BSCI in vitro than the corresponding (R)-enantiomer. It is for this reason that (I') has been studied in most experiments, rather than the isolated (R)-enantiomer or a mixture of the enantiomers. However, the ADME properties are unlikely to be related to the primary pharmacological activity. Indeed, for many compounds the ADME properties of enantiomeric pairs are very similar, since (in many cases) the physical properties of the compound are particularly dominant in determining the in vivo disposition, and the physical properties of enantiomeric pairs are identical.

As a result, we tested whether the (R)-enantiomer shares the particularly excellent ADME properties of (I'). Since the utility of any particular compound depends on both the potency of the primary pharmacological effect(s) and on the disposition of the molecule in vivo (since to be efficacious, the drug molecule must be present at the intended target site(s) at a sufficient concentration to exert its pharmacological effects), then a compound that has lower potency but excellent ADME properties may be more efficacious (or more potent in vivo) than a comparator compound of greater potency but inferior ADME properties.

The isolated (R)-enantiomer of (I) was therefore synthesised (exactly as described herein for the isolated (S)-enantiomer, but replacing the (S)-ornithine starting material with commercially available (R)-ornithine of high stereochemical purity), and the PK properties of this agent, in rat, was determined using the identical methodology described above (see Examples 1, 7 and 8).

Results

The parameters of a simple one-compartment pharmacokinetic model are shown in Table 9. Data for compound (I') from Table 1 above is shown for comparison. It is evident that (R)-(I) shares, to a large extent, the unexpectedly superior ADME properties of (I'). As with (I'), (R)-(I) is also essentially quantitatively orally bioavailable, and achieves an exposure following a single oral dose at 3 mg/kg more than 5-times higher than the next best compound tested to date (see compound (V) in example 1; Table 1).

TABLE 9

Pharmacokinetic parameters for the isolated (R)- and (S)-enantiomers of (I).

| | F (%) | $t^{1/2}$ (mins) | Clearance (ml/min/kg) | Vss (L/kg) | Exposure (min · ng/ml) |
|---|---|---|---|---|---|
| (R)-(I) | 84 | 81 | 8.6 | 0.9 | 295,000 |
| (I') | 69 | 196 | 2.6 | 0.7 | 939,000 |

Oral bioavailability (F, %), dominant plasma half-life ($t^{1/2}$, mins) following intravenous dosing, clearance (ml/min/kg), volume of distribution (Vss, L/kg) and oral exposure (AUC 0-t, min · ng/ml) from a simple one-compartment pharmacokinetic model for each compound, averaged across three rats. In both cases, peak plasma concentration was typically observed by 30 mins, consistent with good absorption.

Although (R)-(I) clearly shares, to a significant extent, the unusually beneficial ADME properties of (I'), there are nevertheless some statistically significant differences. Most marked is the increased plasma clearance (~3-fold higher for (R)-(I) compared with (I')), resulting in a 2-fold shorter plasma half-life following intravenous dosing as well as a 3-fold lower exposure following the single oral dose.

The clearance of (R)-(I) approximates the glomerular filtration rate in rat (typically quoted at 9 ml/min/kg), whereas the clearance of (I') is significantly lower. Once possible interpretation of these findings is that (I') is actively reabsorbed, perhaps in the distal tubule of the nephron, and this reabsorption process is selective for the (S)-enantiomer over the (R)-enantiomer. If, as seems plausible, the unexpected and highly superior ADME properties of (I') are due, in part, to reuptake in the nephron via a transporter capable of distinguishing the (S)-enantiomer from the (R)-enantiomer then it underlines the unpredictability of ADME properties, and further illustrates the non-obviousness of the invention described herein.

Nevertheless, (R)-(I) is clearly also a superior compound according to the present invention (as illustrated by the open circle in FIG. 10, which illustrates that it is closer in ADME properties to (I') than to the general class of acylaminolactams. In conclusion, therefore, both (R)-(I) and (I'), and hence more generally compound (I) is shown to have unexpectedly, and markedly, superior ADME properties compared to other acylaminolactam BSCIs which have been disclosed. Moreover, compound (I') is slightly, but significantly, superior to compound (I) generally, and is therefore preferred.

What is claimed is:

1. A method of treating or ameliorating the symptoms of rheumatoid arthritis by administering to a patient in need thereof an anti-inflammatory amount of a compound of formula (I) or a pharmaceutically acceptable salt thereof, or a pharmaceutically acceptable composition comprising, as active ingredient, a compound of formula (I) or a pharmaceutically acceptable salt thereof, and at least one pharmaceutically acceptable excipient and/or carrier or medicament comprising a compound of formula (I):

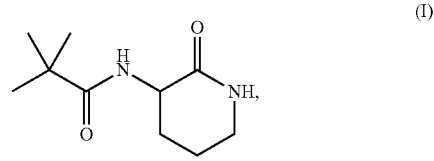

(I)

wherein the symptoms include an adverse inflammatory reaction to an anti-arthritic agent.

2. A method of treating or ameliorating the symptoms of rheumatoid arthritis by administering to a patient in need thereof an anti-inflammatory amount of a compound of formula (I') or a pharmaceutically acceptable salt thereof, or a pharmaceutically acceptable composition comprising, as active ingredient, a compound of formula (I') or a pharmaceutically acceptable salt thereof, and at least one pharmaceutically acceptable excipient and/or carrier or medicament comprising a compound of formula (I'):

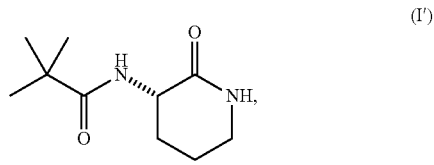

(I')

wherein the symptoms include an adverse inflammatory reaction to an anti-arthritic agent.

* * * * *

UNITED STATES PATENT AND TRADEMARK OFFICE
CERTIFICATE OF CORRECTION

PATENT NO. : 8,853,200 B2
APPLICATION NO. : 12/671785
DATED : October 7, 2014
INVENTOR(S) : Grainger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 706 days.

Signed and Sealed this
Twenty-first Day of June, 2016

Michelle K. Lee
*Director of the United States Patent and Trademark Office*